(12) United States Patent
Miner et al.

(10) Patent No.: US 12,243,638 B1
(45) Date of Patent: Mar. 4, 2025

(54) GENERATING SERVICE OFFERINGS BASED ON ASSOCIATED CONTENT AND HISTORICAL DATA

(71) Applicant: DexCare, Inc., Seattle, WA (US)

(72) Inventors: Madison Cole Miner, Bellingham, WA (US); Eric Andrew Kolve, Seattle, WA (US); Jonathan Peter Manion, Bellingham, WA (US); Robert Imre Gara, Jr., Seattle, WA (US)

(73) Assignee: DexCare, Inc., Seattle, WA (US)

( * ) Notice: Subject to any disclaimer, the term of this patent is extended or adjusted under 35 U.S.C. 154(b) by 0 days.

(21) Appl. No.: 18/615,623

(22) Filed: Mar. 25, 2024

(51) Int. Cl.
| | |
|---|---|
| *G06Q 10/0639* | (2023.01) |
| *G06F 40/40* | (2020.01) |
| *G06Q 30/018* | (2023.01) |
| *G16H 10/60* | (2018.01) |
| *G16H 40/20* | (2018.01) |
| *G16H 50/70* | (2018.01) |

(52) U.S. Cl.
CPC ............. *G16H 40/20* (2018.01); *G16H 10/60* (2018.01); *G16H 50/70* (2018.01)

(58) Field of Classification Search
CPC ......... G16H 40/20; G16H 10/60; G16H 50/70
See application file for complete search history.

(56) References Cited

U.S. PATENT DOCUMENTS

| | | |
|---|---|---|
| 8,145,726 B1 | 3/2012 | Roche et al. |
| 9,372,731 B1 | 6/2016 | Marr et al. |
| 9,380,268 B2 | 6/2016 | Weber et al. |
| 9,402,054 B2 | 7/2016 | Aaron et al. |

(Continued)

FOREIGN PATENT DOCUMENTS

| | | |
|---|---|---|
| CN | 113923441 A | 1/2022 |
| JP | 2016-167676 A | 9/2016 |

(Continued)

OTHER PUBLICATIONS

Tan et al., "From Telemedicine Toe-health: Uncovering New Frontiers of Biomedical Research, Clinical Applications & Public Health Services Delivery" The Journal of Computer Information Systems, vol. 42 No. 5, pp. 7-18, Year: 2002.

(Continued)

*Primary Examiner* — Maroun P Kanaan
(74) *Attorney, Agent, or Firm* — John W. Branch; Branch Partners PLLC

(57) ABSTRACT

Embodiments are directed to generating service offerings based on associated content and historical data. Content from a content panel may be provided. Subjects associated with the content may be determined based on information included in the content. A service category associated with the subjects may be determined based on services provided by a healthcare organization. An offering model may be employed to generate an offering panel based on the service category. The offering model may be evaluated based on monitoring interactions between users and the offering panel. Results of the evaluation may be employed to perform further actions including: designating the offering model for retraining based on the performance metrics; retraining the designated offering model; employing the retrained offering model to generate other offering panels for display to the users; or the like.

28 Claims, 16 Drawing Sheets

(56) References Cited

U.S. PATENT DOCUMENTS

| | | |
|---|---|---|
| 9,497,412 B1 | 11/2016 | Rosenberg |
| 11,595,221 B1 | 2/2023 | Wlodarczyk et al. |
| 11,641,385 B1 | 5/2023 | Ferry et al. |
| 11,838,140 B2 | 12/2023 | Wlodarczyk et al. |
| 11,854,708 B2 | 12/2023 | Streat et al. |
| 11,930,060 B2 | 3/2024 | Ferry et al. |
| 2004/0185785 A1 | 9/2004 | Mir et al. |
| 2006/0271400 A1 | 11/2006 | Clements et al. |
| 2014/0180715 A1 | 6/2014 | Phillips et al. |
| 2014/0313282 A1 | 10/2014 | Ma et al. |
| 2016/0308737 A1 | 10/2016 | Liu et al. |
| 2017/0272485 A1 | 9/2017 | Gordon et al. |
| 2019/0079786 A1 | 3/2019 | Shani et al. |
| 2019/0122760 A1 | 4/2019 | Wang |
| 2019/0333613 A1 | 10/2019 | Zaidi et al. |
| 2020/0222813 A1 | 7/2020 | Baszucki |
| 2020/0357494 A1 | 11/2020 | Kadri et al. |
| 2021/0076001 A1 | 3/2021 | Periyannan et al. |
| 2021/0314526 A1 | 10/2021 | Astarabadi et al. |
| 2021/0319914 A1 | 10/2021 | Roh |
| 2021/0358618 A1 | 11/2021 | Crocker |
| 2021/0399911 A1 | 12/2021 | Jorasch et al. |
| 2021/0400142 A1 | 12/2021 | Jorasch et al. |
| 2021/0406841 A1 | 12/2021 | Chen et al. |
| 2022/0165401 A1 | 5/2022 | Levitt |
| 2022/0215970 A1 | 7/2022 | Trpkovski et al. |
| 2023/0153740 A1* | 5/2023 | Meehan ........... G06Q 10/06395 705/7.41 |
| 2023/0187086 A1 | 6/2023 | Streat et al. |
| 2023/0291592 A1 | 9/2023 | Wlodarczyk et al. |
| 2023/0403314 A1 | 12/2023 | Ferry et al. |
| 2024/0120043 A1* | 4/2024 | Kaushal ................. G16H 10/40 |

FOREIGN PATENT DOCUMENTS

| | | |
|---|---|---|
| WO | 2014/018012 A1 | 1/2014 |
| WO | 2016/019227 A1 | 2/2016 |
| WO | 2023/172390 A1 | 9/2023 |

OTHER PUBLICATIONS

International Search Report and Written Opinion for International Patent Application No. PCT/US2023/013531 mailed Jun. 6, 2023, pp. 1-7.

Office Communication for U.S. Appl. No. 17/551,084 mailed Nov. 1, 2023, pp. 1-22.
Office Communication for U.S. Appl. No. 17/837,218 mailed Mar. 9, 2023, pp. 1-7.
Office Communication for U.S. Appl. No. 17/837,218 mailed Mar. 15, 2023, pp. 1-2.
Office Communication for U.S. Appl. No. 18/114,916 mailed May 23, 2023, pp. 1-9.
Office Communication for U.S. Appl. No. 17/837,218 mailed Nov. 17, 2022, pp. 1-20.
Office Communication for U.S. Appl. No. 17/692,738 mailed Jan. 5, 2023, pp. 1-8.
Office Communication for U.S. Appl. No. 17/837,218 mailed Feb. 9, 2023, pp. 1-5.
Office Communication for U.S. Appl. No. 17/837,218 mailed Aug. 12, 2022, pp. 1-17.
Office Communication for U.S. Appl. No. 17/692,738 mailed Oct. 4, 2022, pp. 1-10.
Office Communication for U.S. Appl. No. 17/692,738 mailed Jun. 13, 2022, pp. 1-9.
Office Communication for U.S. Appl. No. 17/551,084 mailed May 23, 2023, pp. 1-6.
Office Communication for U.S. Appl. No. 17/551,084 mailed Sep. 16, 2022, pp. 1-4.
Office Communication for U.S. Appl. No. 17/551,084 mailed Jul. 1, 2022, pp. 1-59.
Office Communication for U.S. Appl. No. 18/114,916 mailed Sep. 19, 2023, pp. 1-7.
Office Communication for U.S. Appl. No. 17/551,084 mailed Jul. 13, 2023, pp. 1-28.
Office Communication for U.S. Appl. No. 17/551,084 mailed Nov. 15, 2022, pp. 1-61.
Office Communication for U.S. Appl. No. 17/551,084 mailed Mar. 6, 2023, pp. 1-26.
Office Communication for U.S. Appl. No. 18/130,660 mailed Sep. 28, 2023, pp. 1-19.
Office Communication for U.S. Appl. No. 18/130,660 mailed Dec. 14, 2023, pp. 1-4.
Office Communication for U.S. Appl. No. 18/130,660 mailed Jan. 11, 2024, pp. 1-7.
Office Communication for U.S. Appl. No. 18/130,660 mailed Jun. 14, 2023, pp. 1-16.
Office Communication for U.S. Appl. No. 17/551,084 mailed Mar. 14, 2022, pp. 1-52.

* cited by examiner

Content Website 600

602

*Lorem ipsum dolor sit amet, consectetur adipiscing elit, sed do eiusmod tempor incididunt ut labore et dolore magna aliqua. Ut enim ad minim veniam, quis nostrud exercitation ullamco laboris nisi ut aliquip ex ea commodo consequat. Duis ante irure dolor in reprehenderit in voluptate velit esse cillum dolore eu fugiat nulla pariatur. Excepteur sint occaecat cupidatat non proident, sunt in culpa qui officia deserunt mollit anim id est laborum*

*Lorem ipsum dolor sit amet, consectetur adipiscing elit, sed do eiusmod tempor incididunt ut labore et dolore magna aliqua. Ut enim ad minim veniam, quis nostrud exercitation ullamco laboris nisi ut aliquip ex ea commodo consequat. Duis ante irure dolor in reprehenderit in voluptate velit esse cillum dolore eu fugiat nulla pariatur. Excepteur sint occaecat cupidatat non proident, sunt in culpa qui officia deserunt mollit anim id est laborum*

604

Speak with a provider now

Next available visit

| Date | Time | Duration |
|---|---|---|
| 12/01/2020 | 10:00 am | 45 min |

*Fig. 6*

GENERATING SERVICE OFFERINGS BASED ON ASSOCIATED CONTENT AND HISTORICAL DATA

TECHNICAL FIELD

The present invention relates generally to managing healthcare services, and more particularly, but not exclusively, to generating service offerings based on associated content and historical data.

BACKGROUND

Providing healthcare services often requires complex relationships between disparate stakeholders, including, patients, patient guardians, providers, provider organizations, third-party payors, or the like. In some cases, providing effective service may require responsive communication among and between the various stakeholders. Further, provider organizations may expend significant resources managing fluid communication or shared responsibilities among the various parties associated with providing healthcare services. In some cases, determining the service requirements for patients or allocating appropriate provider resources to meet the service requirements may be hindered by communication breakdowns or other hard-to-see issues related to the complexity of relationship between involved parties. Often healthcare organizations or others may provide online healthcare content, such as articles, blog posts, podcasts, scientific papers, medical reference information, or the like that their patients or the general public may access. In some cases, patient specific or service visit specific information may be included alongside or embedded in this content. However, determining relevant offerings or associating such offerings with particular content may require expensive manual intervention. Thus, it is with respect to these considerations and others that the present invention has been made.

BRIEF DESCRIPTION OF THE DRAWINGS

Non-limiting and non-exhaustive embodiments of the present innovations are described with reference to the following drawings. In the drawings, like reference numerals refer to like parts throughout the various figures unless otherwise specified. For a better understanding of the described innovations, reference will be made to the following Detailed Description of Various Embodiments, which is to be read in association with the accompanying drawings, wherein:

FIG. 6 illustrates a logical schematic of a content panel that includes service offerings based on associated content and historical data in accordance with one or more of the various embodiments;

DETAILED DESCRIPTION OF VARIOUS EMBODIMENTS

Figure 1:
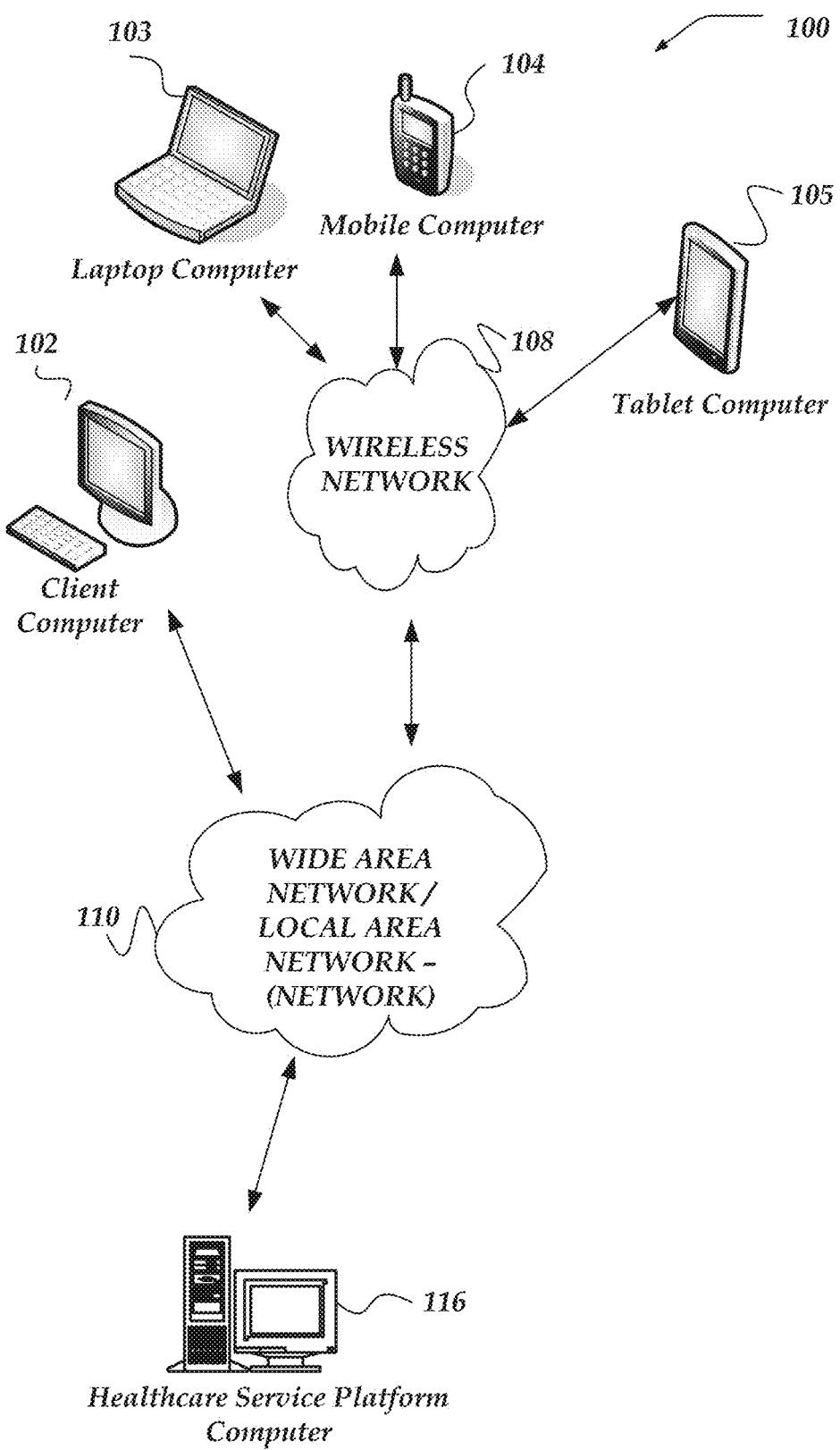
FIG. 1 illustrates a system environment in which various embodiments may be implemented.

Various embodiments now will be described more fully hereinafter with reference to the accompanying drawings, which form a part hereof, and which show, by way of illustration, specific exemplary embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media or devices. Accordingly, the various embodiments may take the form of an entirely hardware embodiment, an entirely software embodiment or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

For example, embodiments, the following terms are also used herein according to the corresponding meaning, unless the context clearly dictates otherwise.

As used herein the term, "engine" refers to logic embodied in hardware or software instructions, which can be written in a programming language, such as C, C++, Objective-C, COBOL, Java™, PHP, Perl, Python, R, Julia, JavaScript, Ruby, VBScript, Microsoft .NET™ languages such as C#, or the like. An engine may be compiled into executable programs or written in interpreted programming languages. Software engines may be callable from other engines or from themselves. Engines described herein refer to one or more logical modules that can be merged with other engines or applications, or can be divided into sub-engines. The engines can be stored in non-transitory computer-readable mediums or computer storage devices and be stored on and executed by one or more general purpose computers, thus creating a special purpose computer configured to provide the engine.

As used herein, the term "provider" refers to a professional care provider that may be assigned to provide care services for a patient visit. Providers may include physicians, physician assistants, nurse practitioners, nurses, medical assistants, nursing assistants, physical therapists, or the like. In many cases, providers may be individual service providers. In some cases, providers may be third party organizations rather than individuals.

As used herein, the term "provider organization" refers to an organization that provides professional care services to patients. Provider organizations may include large nationwide healthcare networks, state-wide networks, private clinics, independent hospitals, urgent care networks, or the like. Generally, provider organizations represent one or more providers and provide the facilities or administrative support that enable care services to be provided to patients. In some cases, one large provider organization may be comprised of a federation of other smaller provider organizations.

As used herein, the term "patient" refers to person seeking care services from a provider organization or provider. In some cases, a guardian may be providing information or authorizing care for a patient.

As used herein, the term "patient visit profile" refers to one or more data structures that include one or more fields that represent characteristics of a patient and a visit. Patient visit profiles may include fields for patient identity, patient demographics, payor information, or the like. Also, patient visit profiles may include visit information, such as, reason for visit, assigned provider, date of visit, duration of visit, visit resolution information, or the like. Patient visit profiles may provide regularized input to matching engines that may match patient visit profiles with providers. Some or all of the attributed included patient visit profiles may be vectorized or otherwise formatted to be suitable for evaluating with matching models to generate matching scores for matching providers with visits.

As used herein, the term "service offering" refers to data structures, user interfaces, or the like, that represent an offering of a service to a user or patient. Service offerings may include information about available appointments, available service providers, service types, locations, or the like.

As used herein, the terms "large language model," or "LLM" refer to data structures, programs, or the like, that may be trained or designed to perform a variety of natural language processing tasks. Typically, LLMs may generate text responses in response to text-based prompts. Often, LLMs may be considered to be neural networks that have been trained on large collections of natural language source documents. Accordingly, in some cases, LLMs may be trained to generate predictive responses based on provided prompts. LLM prompts may include context information, examples, or the like, that may enable LLMs to generate responses directed to specific queries or particular problems that go beyond conventional NLP.

As used herein, the term "prompt" refers to one or more data structures that contain or represent prompt information that may be provided to LLMs.

As used herein, the term "content model" refers to one or more data structures that may include machine learning based models, heuristics, filters, pattern matching, or the like that may identify or extract content information from content sources such as web pages, audio podcasts, videos, or other digitized media. In some cases, there may be different types of content models that may be directed to different types of content or content media.

As used herein, the term "subject model" refers to one or more data structures that may include machine learning based models, heuristics, filters, pattern matching, or the like that may predict or infer one or more subjects of provided content information. In some cases, predicting content subjects may include generating prompts that are submitted to large language models or other generative artificial intelligence systems such that responses to the prompts may include information associated with one or more subjects included in the content. In some cases, there may be different types of subject models that may be directed to different types of content, content media, problem domains, locations, or the like.

As used herein, the term "subject-category model" refers to one or more data structures that may include machine learning based models, heuristics, filters, pattern matching, natural language processing, or the like that may map subjects determined from content to one or more relevant service categories. In some cases, inferring subject-category associations may include generating prompts that are submitted to large language models or other generative artificial intelligence systems such that responses to the prompts may include information for infer one or more service categories based on the provide subject information. In some cases, there may be different types of subject-category models that may be directed to different types of provider organizations, medical specialties, standard or customized ontologies, or the like.

As used herein, the term "training model" refers to one or more data structures that may include machine learning based models, heuristics, filters, pattern matching, natural language processing, or the like that may be configured to train or evaluate the training for offering models being trained or retrained. In some cases, there may be different types of training models that may be directed to different types of provider organizations, medical specialties, organization/provider preferences, or the like.

As used herein, the term "offering model" refers to one or more data structures that may include machine learning based models, heuristics, filters, pattern matching, or the like that may predict or infer one or more characteristics or features of one or more service offerings that may be correlated with content. In some cases, generating offering information may include generating prompts that are submitted to large language models or other generative artificial intelligence systems such that responses to the prompts may include information for generating offering tailored for content or content user. In some cases, there may be different types of offering models that may be directed to different types of content, content media, user types, patients, problem domains, locations, or the like.

As used herein, the terms "input record," or "input data" refer to one or more data structures that include fields, items, or the like, that may be provided to offering models. Input records may include information, such as service category, or the like, that may be used by offering models to generate offering profiles.

As used herein, the term "offering profile" refers to one or more data structures that include fields, items, values, or the like, generated by offering models in response to input records. Offering profiles may be employed to determine one or more characteristics or offering panels that may be generated and presented to users.

As used herein, the term "offering panel" refers to region within a graphical user interface (GUI) that has a defined geometry (e.g., x, y, z-order) within the GUI. Panels may be arranged to display information to users or to host one or more interactive controls associated with healthcare visits (or other healthcare services) offered to users of patients. The geometry or styles associated with panels may be defined using configuration information, including information included or declared in offering profiles.

As used herein, the term "matching model" refers to one or more data structures, data, instructions, or the like, that may be employed to match providers with visits based on various provided inputs including patient visit profiles. In some cases, matching models may be comprised of one or more sub-models, that may include one or more heuristics, filters, rules, trained machine learning models, or the like.

As used herein, the terms "electronic medical record," or "EMR" refer to digital records that include health information of an individual.

As used herein, the term, "configuration information" refers to information that may include rule-based policies, pattern matching, scripts, computer readable instructions, or the like, that may be provided from various sources, including, configuration files, databases, user input, built-in defaults, or the like, or combination thereof. In some cases, configuration information may include or reference information stored in other systems or services, such as, configuration management databases, Lightweight Directory Access Protocol (LDAP) servers, name services, public key infrastructure services, or the like.

The following briefly describes embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, various embodiments are directed to generating service offerings based on associated content and historical data. In one or more of the various embodiments, content from a content panel may be determined based on one or more of a markup language, an encoding, a format associated with the content panel, or the like.

In one or more of the various embodiments, one or more subjects associated with the content may be determined based on information included in the content and one or more evaluations of the content by a subject model.

In one or more of the various embodiments, a service category associated with one or more subjects may be determined based on one or more services provided by a healthcare organization.

In one or more of the various embodiments, an offering model may be employed to generate an offering panel based on the service category and an availability of the one or more services such that the offering panel displays information associated with an available service. In some embodiments the offering model may include one or more machine learning models.

In one or more of the various embodiments, the offering model may be evaluated based on monitoring one or more interactions between one or more of users and the offering panel.

In one or more of the various embodiments, one or more results of the evaluation may be employed to perform further actions including: designating the offering model for retraining based on the one or more performance metrics falling below a threshold value; retraining the designated offering model based on one or more other metrics associated with one or more other offering models and a training model such that the training model includes one or more of a machine learning model or a large language model; employing the retrained offering model to generate one or more other offering panels for display to the one or more users; or the like.

In one or more of the various embodiments, the content in the content panel may be modified to include one or more links or references to the offering panel such that activating the link or reference may display the offering panel separate from the content panel.

In one or more of the various embodiments, generating the offering panel may include: determining a portion of the one or more users that may be patients of the healthcare organization based on authenticating the portion of the one or more users with the healthcare organization; determining patient information for the authenticated portion of the one or more users from the healthcare organization such that the patient information may include one or more of demographic information, a date of a previous visit, insurance information, a provider visited during a previous visit, a service category associated with a previous visit, a patient profile, or the like; providing the patient information to the offering model; or the like.

In one or more of the various embodiments, determining the one or more subjects associated with the content may include: generating a prompt that includes one or more portions of the content for evaluation by the subject model that includes one or more large language models; determining the one or more subjects based on a response provided by the subject model; or the like.

In one or more of the various embodiments, determining the service category associated with the one or more subjects may include: determining a plurality of service categories based on a plurality of services offered by the healthcare organization; employing a subject-category model to determine the plurality of service categories based on one or more matches of the one or more subjects with the one or more service categories; or the like.

In one or more of the various embodiments, generating the offering panel may include: determining one or more available services associated with the service category; prioritizing the one or more available services based on one or more a type of visit, an availability of providers, a utilization of providers, a location of a clinic, or the like, such that the type of visit may include one or more of a virtual-visit, an in-person visit, or the like; generating one or more user interface controls that may enable the user to request a visit associated with the one or more the available services such that the one or more available services may be sorted or redacted based on the prioritization of the one or more available services; or the like.

In one or more of the various embodiments, one or more non-deficient offering panels may be determined based on one or more interaction metrics that may exceed one or more defined threshold values; determining input data and one or more offering profiles associated with the one or more non-deficient offering panels; updating training data to include the determined input data and determined one or more offering profiles; employing the updated training data to retrain the offering model that is designated for retraining; or the like.

Illustrated Operating Environment

FIG. 1 shows components of one embodiment of an environment in which embodiments of the invention may be practiced. Not all of the components may be required to practice the invention, and variations in the arrangement and type of the components may be made without departing from the spirit or scope of the invention. As shown, system 100 of FIG. 1 includes local area networks (LANs)/wide area networks (WANs)—(network) 110, wireless network 108, client computers 102-105, healthcare service platform computer 116, or the like.

At least one embodiment of client computers 102-105 is described in more detail below in conjunction with FIG. 2. In one embodiment, at least some of client computers 102-105 may operate over one or more wired or wireless networks, such as networks 108, or 110. Generally, client computers 102-105 may include virtually any computer capable of communicating over a network to send and receive information, perform various online activities, offline actions, or the like. In one embodiment, one or more of client computers 102-105 may be configured to operate within a business or other entity to perform a variety of services for the business or other entity. For example, client computers 102-105 may be configured to operate as a web server, firewall, client application, media player, mobile telephone, game console, desktop computer, or the like. However, client computers 102-105 are not constrained to these services and may also be employed, for example, as for end-user computing in other embodiments. It should be recognized that more or less client computers (as shown in FIG. 1) may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or the like. In some embodiments, client computers 102-105 may include virtually any portable computer capable of connecting to another computer and receiving information such as, laptop computer 103, mobile computer 104, tablet computers 105, or the like. However, portable computers are not so limited and may also include other portable computers such as cellular telephones, display pagers, radio frequency (RF) devices, infrared (IR) devices, Personal Digital Assistants (PDAs), handheld computers, wearable computers, integrated devices combining one or more of the preceding computers, or the like. As such, client computers 102-105 typically range widely in terms of capabilities and features. Moreover, client computers 102-105 may access various computing applications, including a browser, or other web-based application.

A web-enabled client computer may include a browser application that is configured to send requests and receive responses over the web. The browser application may be configured to receive and display graphics, text, multimedia, and the like, employing virtually any web-based language. In one embodiment, the browser application is enabled to employ JavaScript, HyperText Markup Language (HTML), extensible Markup Language (XML), JavaScript Object Notation (JSON), Cascading Style Sheets (CSS), or the like, or combination thereof, to display and send a message. In one embodiment, a user of the client computer may employ the browser application to perform various activities over a network (online). However, another application may also be used to perform various online activities.

Client computers 102-105 also may include at least one other client application that is configured to receive or send content between another computer. The client application may include a capability to send or receive content, or the like. The client application may further provide information that identifies itself, including a type, capability, name, and the like. In one embodiment, client computers 102-105 may uniquely identify themselves through any of a variety of mechanisms, including an Internet Protocol (IP) address, a phone number, Mobile Identification Number (MIN), an electronic serial number (ESN), a client certificate, or other device identifier. Such information may be provided in one or more network packets, or the like, sent between other client computers, healthcare service platform computer 116, or other computers.

Client computers 102-105 may further be configured to include a client application that enables an end-user to log into an end-user account that may be managed by another computer, such as healthcare service platform computer 116, or the like. Such an end-user account, in one non-limiting example, may be configured to enable the end-user to manage one or more online activities, including in one non-limiting example, project management, software development, system administration, configuration management, search activities, social networking activities, browse various websites, communicate with other users, or the like. Also, client computers may be arranged to enable users to display reports, interactive user-interfaces, results provided by healthcare service platform computer 116, or the like. Wireless network 108 is configured to couple client computers 103-105 and its components with network 110. Wireless network 108 may include any of a variety of wireless sub-networks that may further overlay stand-alone ad-hoc networks, and the like, to provide an infrastructure-oriented connection for client computers 103-105. Such sub-networks may include mesh networks, Wireless LAN (WLAN) networks, cellular networks, and the like. In one embodiment, the system may include more than one wireless network.

Wireless network 108 may further include an autonomous system of terminals, gateways, routers, and the like connected by wireless radio links, and the like. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G) 5th (5G) generation radio access for cellular systems, WLAN, Wireless Router (WR) mesh, and the like. Access technologies such as 2G, 3G, 4G, 5G, and future access networks may enable wide area coverage for mobile computers, such as client computers 103-105 with various degrees of mobility. In one non-limiting example, wireless network 108 may enable a radio connection through a radio network access such as Global System for Mobile communication (GSM), General Packet Radio Services (GPRS), Enhanced Data GSM Environment (EDGE), code division multiple access (CDMA), time division multiple access (TDMA), Wideband Code Division Multiple Access (WCDMA), High Speed Downlink Packet Access (HSDPA), Long Term Evolution (LTE), and the like. In essence, wireless network 108 may include virtually any wireless communication mechanism by which information may travel between client computers 103-105 and another computer, network, a cloud-based network, a cloud instance, or the like.

Network 110 is configured to couple network computers with other computers, including, healthcare service platform computer 116, client computers 102-105 through wireless network 108, or the like. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, Ethernet port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including without limit, for example, DS-0, DS-1, DS-2, DS-3, DS-4, OC-3, OC-12, OC-48, or the like. Furthermore, remote computers and other related electronic devices could be remotely connected to either LANs or WANs via a modem and temporary telephone link. In one embodiment, network 110 may be configured to transport information using one or more network protocols, such as Internet Protocol (IP).

Additionally, communication media typically embodies computer readable instructions, data structures, program modules, or other transport mechanisms and includes any information non-transitory delivery media or transitory delivery media. By way of example, communication media includes wired media such as twisted pair, coaxial cable, fiber optics, wave guides, and other wired media and wireless media such as acoustic, RF, infrared, and other wireless media.

One embodiment of healthcare service platform computer 116 is described in more detail below in conjunction with FIG. 3. Although FIG. 1 illustrates healthcare service platform computer 116 as a single computer, the innovations or embodiments are not so limited. For example, one or more functions of healthcare service platform computer 116, or the like, may be distributed across one or more distinct network computers. Moreover, in one or more embodiments, healthcare service platform computer 116 may be implemented using a plurality of network computers. Further, in one or more of the various embodiments, healthcare service platform computer 116 may be implemented using one or more cloud instances in one or more cloud networks. Accordingly, these innovations and embodiments are not to be construed as being limited to a single environment, and other configurations, and other architectures are also envisaged.

Illustrative Client Computer

Figure 2:
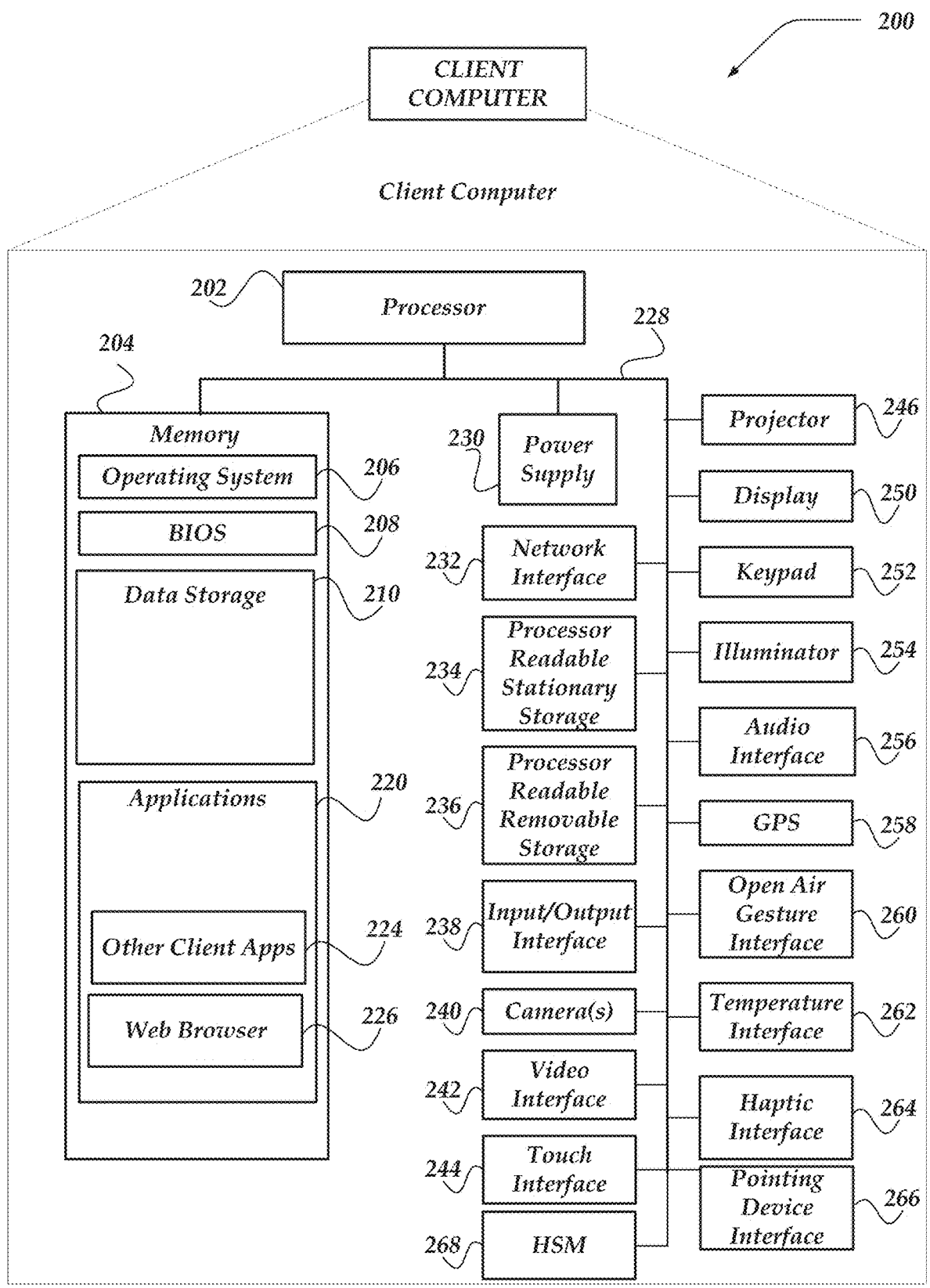
FIG. 2 illustrates a schematic embodiment of a client computer.

FIG. 2 shows one embodiment of client computer 200 that may include many more or less components than those shown. Client computer 200 may represent, for example, at least one embodiment of mobile computers or client computers shown in FIG. 1.

Client computer 200 may include processor 202 in communication with memory 204 via bus 228. Client computer 200 may also include power supply 230, network interface 232, audio interface 256, display 250, keypad 252, illuminator 254, video interface 242, input/output interface 238, haptic interface 264, global positioning systems (GPS) receiver 258, open air gesture interface 260, temperature interface 262, camera(s) 240, projector 246, pointing device interface 266, processor-readable stationary storage device 234, and processor-readable removable storage device 236. Client computer 200 may optionally communicate with a base station (not shown), or directly with another computer. And in one embodiment, although not shown, a gyroscope may be employed within client computer 200 for measuring or maintaining an orientation of client computer 200.

Power supply 230 may provide power to client computer 200. A rechargeable or non-rechargeable battery may be used to provide power. The power may also be provided by an external power source, such as an AC adapter or a powered docking cradle that supplements or recharges the battery.

Network interface 232 includes circuitry for coupling client computer 200 to one or more networks, and is constructed for use with one or more communication protocols and technologies including, but not limited to, protocols and technologies that implement any portion of the OSI model for mobile communication (GSM), CDMA, time division multiple access (TDMA), UDP, TCP/IP, SMS, MMS, GPRS, WAP, UWB, WiMax, SIP/RTP, GPRS, EDGE, WCDMA, LTE, UMTS, OFDM, CDMA2000, EV-DO, HSDPA, or any of a variety of other wireless communication protocols. Network interface 232 is sometimes known as a transceiver, transceiving device, or network interface card (NIC).

Audio interface 256 may be arranged to produce and receive audio signals such as the sound of a human voice. For example, audio interface 256 may be coupled to a speaker and microphone (not shown) to enable telecommunication with others or generate an audio acknowledgement for some action. A microphone in audio interface 256 can also be used for input to or control of client computer 200, e.g., using voice recognition, detecting touch based on sound, and the like.

Display 250 may be a liquid crystal display (LCD), gas plasma, electronic ink, light emitting diode (LED), Organic LED (OLED) or any other type of light reflective or light transmissive display that can be used with a computer. Display 250 may also include a touch interface 244 arranged to receive input from an object such as a stylus or a digit from a human hand, and may use resistive, capacitive, surface acoustic wave (SAW), infrared, radar, or other technologies to sense touch or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or the like. For example, video interface 242 may be coupled to a digital video camera, a web-camera, or the like. Video interface 242 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial, or a keyboard. Keypad 252 may also include command buttons that are associated with selecting and sending images.

Illuminator 254 may provide a status indication or provide light. Illuminator 254 may remain active for specific periods of time or in response to event messages. For example, when illuminator 254 is active, it may backlight the buttons on keypad 252 and stay on while the client computer is powered. Also, illuminator 254 may backlight these buttons in various patterns when particular actions are performed, such as dialing another client computer. Illuminator 254 may also cause light sources positioned within a transparent or translucent case of the client computer to illuminate in response to actions.

Further, client computer 200 may also comprise hardware security module (HSM) 268 for providing additional tamper resistant safeguards for generating, storing or using security/cryptographic information such as, keys, digital certificates, passwords, passphrases, two-factor authentication information, or the like. In some embodiments, hardware security modules may be employed to support one or more standard public key infrastructures (PKI), and may be employed to generate, manage, or store keys pairs, or the like. In some embodiments, HSM 268 may be a stand-alone computer, in other cases, HSM 268 may be arranged as a hardware card that may be added to a client computer.

Client computer 200 may also comprise input/output interface 238 for communicating with external peripheral devices or other computers such as other client computers and network computers. The peripheral devices may include an audio headset, virtual reality headsets, display screen glasses, remote speaker system, remote speaker and microphone system, and the like. Input/output interface 238 can utilize one or more technologies, such as Universal Serial Bus (USB), Infrared, WiFi, WiMax, Bluetooth™, and the like.

Input/output interface 238 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect or measure data that is external to client computer 200.

Haptic interface 264 may be arranged to provide tactile feedback to a user of the client computer. For example, the haptic interface 264 may be employed to vibrate client computer 200 in a particular way when another user of a computer is calling. Temperature interface 262 may be used to provide a temperature measurement input or a temperature changing output to a user of client computer 200. Open air gesture interface 260 may sense physical gestures of a user of client computer 200, for example, by using single or stereo video cameras, radar, a gyroscopic sensor inside a computer held or worn by the user, or the like. Camera 240 may be used to track physical eye movements of a user of client computer 200.

GPS transceiver 258 can determine the physical coordinates of client computer 200 on the surface of the Earth, which typically outputs a location as latitude and longitude values. GPS transceiver 258 can also employ other geopositioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 258 can determine a physical location for client computer 200. In one or more embodiments, however, client computer 200 may, through other components, provide other information that may be employed to determine a physical location of the client computer, including for example, a Media Access Control (MAC) address, IP address, and the like.

Human interface components can be peripheral devices that are physically separate from client computer 200, allowing for remote input or output to client computer 200. For example, information routed as described here through human interface components such as display 250 or keyboard 252 can instead be routed through network interface 232 to appropriate human interface components located remotely. Examples of human interface peripheral components that may be remote include, but are not limited to, audio devices, pointing devices, keypads, displays, cameras, projectors, and the like. These peripheral components may communicate over a Pico Network such as Bluetooth™, Zigbee™ and the like. One non-limiting example of a client computer with such peripheral human interface components is a wearable computer, which might include a remote pico projector along with one or more cameras that remotely communicate with a separately located client computer to sense a user's gestures toward portions of an image projected by the pico projector onto a reflected surface such as a wall or the user's hand.

A client computer may include web browser application 226 that is configured to receive and to send web pages, web-based messages, graphics, text, multimedia, and the like. The client computer's browser application may employ virtually any programming language, including a wireless application protocol message (WAP), and the like. In one or more embodiment, the browser application is enabled to employ Handheld Device Markup Language (HDML), Wireless Markup Language (WML), WMLScript, JavaScript, Standard Generalized Markup Language (SGML), HyperText Markup Language (HTML), extensible Markup Language (XML), HTML5, and the like.

Memory 204 may include RAM, ROM, or other types of memory. Memory 204 illustrates an example of computer-readable storage media (devices) for storage of information such as computer-readable instructions, data structures, program modules or other data. Memory 204 may store BIOS 208 for controlling low-level operation of client computer 200. The memory may also store operating system 206 for controlling the operation of client computer 200. It will be appreciated that this component may include a general-purpose operating system such as a version of UNIX®, or Linux®, or a specialized client computer communication operating system such as Windows Phone™, or the Symbian® operating system. The operating system may include, or interface with a Java virtual machine module that enables control of hardware components or operating system operations via Java application programs.

Memory 204 may further include one or more data storage 210, which can be utilized by client computer 200 to store, among other things, applications 220 or other data. For example, data storage 210 may also be employed to store information that describes various capabilities of client computer 200. The information may then be provided to another device or computer based on any of a variety of methods, including being sent as part of a header during a communication, sent upon request, or the like. Data storage 210 may also be employed to store social networking information including address books, buddy lists, aliases, user profile information, or the like. Data storage 210 may further include program code, data, algorithms, and the like, for use by a processor, such as processor 202 to execute and perform actions. In one embodiment, at least some of data storage 210 might also be stored on another component of client computer 200, including, but not limited to, non-transitory processor-readable removable storage device 236, processor-readable stationary storage device 234, or even external to the client computer.

Applications 220 may include computer executable instructions which, when executed by client computer 200, transmit, receive, or otherwise process instructions and data. Applications 220 may include, for example, other client applications 224, web browser 226, or the like. Client computers may be arranged to exchange communications, such as, queries, searches, messages, notification messages, event messages, alerts, performance metrics, log data, API calls, or the like, combination thereof, with healthcare service platforms. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth.

Additionally, in one or more embodiments (not shown in the figures), client computer 200 may include one or more embedded logic hardware devices instead of CPUs, such as, an Application Specific Integrated Circuit (ASIC), Field Programmable Gate Array (FPGA), Programmable Array Logic (PAL), or the like, or combination thereof. The embedded logic hardware devices may directly execute embedded logic to perform actions. Also, in one or more embodiments (not shown in the figures), client computer 200 may include one or more hardware microcontrollers instead of CPUs. In one or more embodiments, the microcontrollers may directly execute their own embedded logic to perform actions and access their own internal memory and their own external Input and Output Interfaces (e.g., hardware pins or wireless transceivers) to perform actions, such as System On a Chip (SOC), or the like.

Illustrative Network Computer

Figure 3:
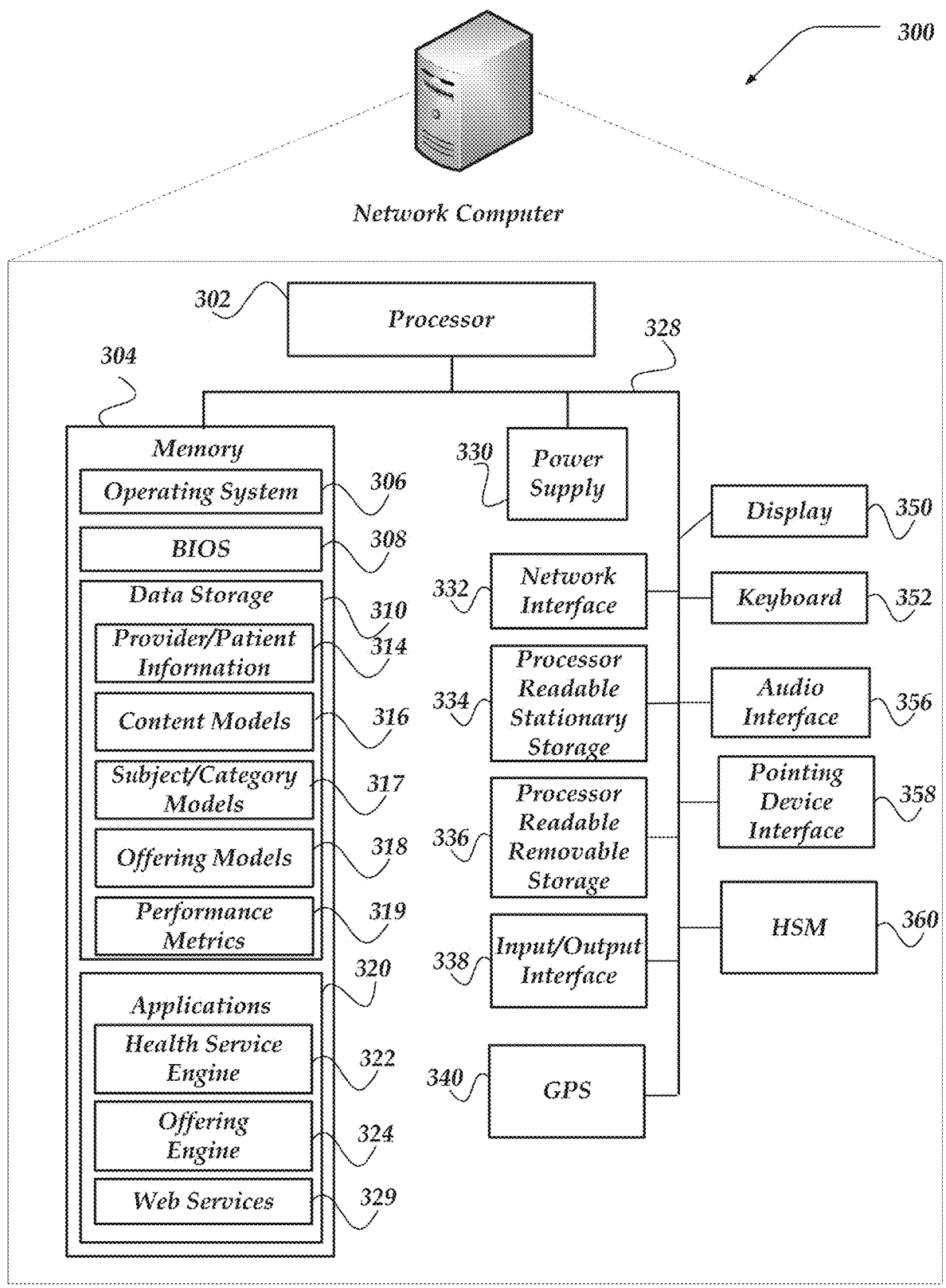
FIG. 3 illustrates a schematic embodiment of a network computer.

FIG. 3 shows one embodiment of network computer 300 that may be included in a system implementing at least one of the various embodiments. Network computer 300 may include many more or less components than those shown in FIG. 3. However, the components shown are sufficient to disclose an illustrative embodiment for practicing these innovations. Network computer 300 may represent, for example, one embodiment of healthcare service platform computer 116 of FIG. 1.

As shown in the figure, network computer 300 includes a processor 302 that may be in communication with a memory 304 via a bus 328. In some embodiments, processor 302 may include one or more hardware processors, or one or more processor cores. In some cases, one or more of the one or more processors may be specialized processors designed to perform one or more specialized actions, such as those described herein. Network computer 300 also includes a power supply 330, network interface 332, audio interface 356, display 350, keyboard 352, input/output interface 338, processor-readable stationary storage device 334, and processor-readable removable storage device 336. Power supply 330 provides power to network computer 300.

Network interface 332 includes circuitry for coupling network computer 300 to one or more networks, and is constructed for use with one or more communication protocols and technologies including, but not limited to, protocols and technologies that implement any portion of the Open Systems Interconnection model (OSI model), global system for mobile communication (GSM), code division multiple access (CDMA), time division multiple access (TDMA), user datagram protocol (UDP), transmission control protocol/Internet protocol (TCP/IP), Short Message Service (SMS), Multimedia Messaging Service (MMS), general packet radio service (GPRS), WAP, ultra-wide band (UWB), IEEE 802.16 Worldwide Interoperability for Microwave Access (WiMax), Session Initiation Protocol/Real-time Transport Protocol (SIP/RTP), or any of a variety of other wired and wireless communication protocols. Network interface 332 is sometimes known as a transceiver, transceiving device, or network interface card (NIC). Network computer 300 may optionally communicate with a base station (not shown), or directly with another computer.

Audio interface 356 is arranged to produce and receive audio signals such as the sound of a human voice. For example, audio interface 356 may be coupled to a speaker and microphone (not shown) to enable telecommunication with others or generate an audio acknowledgement for some action. A microphone in audio interface 356 can also be used for input to or control of network computer 300, for example, using voice recognition.

Display 350 may be a liquid crystal display (LCD), gas plasma, electronic ink, light emitting diode (LED), Organic LED (OLED) or any other type of light reflective or light transmissive display that can be used with a computer. In some embodiments, display 350 may be a handheld projector or pico projector capable of projecting an image on a wall or other object.

Network computer 300 may also comprise input/output interface 338 for communicating with external devices or computers not shown in FIG. 3. Input/output interface 338 can utilize one or more wired or wireless communication technologies, such as USB™, Firewire™, WiFi, WiMax, Thunderbolt™, Infrared, Bluetooth™, Zigbee™, serial port, parallel port, and the like.

Also, input/output interface 338 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect or measure data that is external to network computer 300. Human interface components can be physically separate from network computer 300, allowing for remote input or output to network computer 300. For example, information routed as described here through human interface components such as display 350 or keyboard 352 can instead be routed through the network interface 332 to appropriate human interface components located elsewhere on the network. Human interface components include any component that allows the computer to take input from, or send output to, a human user of a computer. Accordingly, pointing devices such as mice, styluses, track balls, or the like, may communicate through pointing device interface 358 to receive user input.

GPS transceiver 340 can determine the physical coordinates of network computer 300 on the surface of the Earth, which typically outputs a location as latitude and longitude values. GPS transceiver 340 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of network computer 300 on the surface of the Earth. It is understood that under different conditions, GPS transceiver 340 can determine a physical location for network computer 300. In one or more embodiments, however, network computer 300 may, through other components, provide other information that may be employed to determine a physical location of the client computer, including for example, a Media Access Control (MAC) address, IP address, and the like.

In at least one of the various embodiments, applications, such as, operating system 306, healthcare service engine 322, offering engine 324, web services 329, or the like, may be arranged to employ geo-location information to select one or more localization features, such as, time zones, languages, currencies, calendar formatting, or the like. Localization features may be used when scheduling/visit information, provider availability, patient preferences, user-interfaces, generating reports, as well as internal processes or databases. In at least one of the various embodiments, geo-location information used for selecting localization information may be provided by GPS 340. Also, in some embodiments, geolocation information may include information provided using one or more geolocation protocols over the networks, such as, wireless network 108 or network 111.

Memory 304 may include Random Access Memory (RAM), Read-Only Memory (ROM), or other types of memory. Memory 304 illustrates an example of computer-readable storage media (devices) for storage of information such as computer-readable instructions, data structures, program modules or other data. Memory 304 stores a basic input/output system (BIOS) 308 for controlling low-level operation of network computer 300. The memory also stores an operating system 306 for controlling the operation of network computer 300. It will be appreciated that this component may include a general-purpose operating system such as a version of UNIX, or Linux® or a specialized operating system such as Microsoft Corporation's Windows® operating system, or the Apple Corporation's IOS® operating system. The operating system may include, or interface with a Java virtual machine (JVM) or other run-time engines that enable control of hardware components or operating system operations via application programs executed the JVM or other run-time execution engines.

Memory 304 may further include one or more data storage 310, which can be utilized by network computer 300 to store, among other things, applications 320 or other data. For example, data storage 310 may also be employed to store information that describes various capabilities of network computer 300. The information may then be provided to another device or computer based on any of a variety of methods, including being sent as part of a header during a communication, sent upon request, or the like. Data storage 310 may also be employed to store social networking information including address books, buddy lists, aliases, user profile information, or the like. Data storage 310 may further include program code, data, algorithms, and the like, for use by a processor, such as processor 302 to execute and perform actions such as those actions described below. In one embodiment, at least some of data storage 310 might also be stored on another component of network computer 300, including, but not limited to, non-transitory media inside processor-readable removable storage device 336, processor-readable stationary storage device 334, or any other computer-readable storage device within network computer 300, or even external to network computer 300. Data storage 310 may include, for example, provider/patient information, 314, content models 316, subject/category models 317, offering models 318, performance metrics 319, or the like.

Applications 320 may include computer executable instructions which, when executed by network computer 300, transmit, receive, or otherwise process messages (e.g., SMS, Multimedia Messaging Service (MMS), Instant Message (IM), email, or other messages), audio, video, and enable telecommunication with another user of another mobile computer. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth. Applications 320 may include healthcare service engine 322, offering engine 324, web services 329, or the like, that may be arranged to perform actions for embodiments described below. In one or more of the various embodiments, one or more of the applications may be implemented as modules or components of another application. Further, in one or more of the various embodiments, applications may be implemented as operating system extensions, modules, plugins, or the like.

Furthermore, in one or more of the various embodiments, healthcare service engine 322, offering engine 324, web services 329, or the like, may be operative in a cloud-based computing environment. In one or more of the various embodiments, these applications, and others, that comprise a healthcare service platform may be executing within virtual machines or virtual servers that may be managed in a cloud-based based computing environment. In one or more of the various embodiments, in this context the applications may flow from one physical network computer within the cloud-based environment to another depending on performance and scaling considerations automatically managed by the cloud computing environment. Likewise, in one or more of the various embodiments, virtual machines or virtual servers dedicated to healthcare service engine 322, offering engine 324, web services 329, or the like, may be provisioned and de-commissioned automatically.

Also, in one or more of the various embodiments, healthcare service engine 322, offering engine 324, web services 329, or the like, may be located in virtual servers running in a cloud-based computing environment rather than being tied to one or more specific physical network computers. Likewise, in some embodiments, one or more of healthcare service platform 322, offering engine 324, web services 329, or the like, may be configured to execute in a container-based environment.

Further, network computer 300 may also comprise hardware security module (HSM) 360 for providing additional tamper resistant safeguards for generating, storing or using security/cryptographic information such as, keys, digital certificates, passwords, passphrases, two-factor authentication information, or the like. In some embodiments, hardware security modules may be employed to support one or more standard public key infrastructures (PKI), and may be employed to generate, manage, or store keys pairs, or the like. In some embodiments, HSM 360 may be a stand-alone network computer, in other cases, HSM 360 may be arranged as a hardware card that may be installed in a network computer.

Additionally, in one or more embodiments (not shown in the figures), network computer 300 may include one or more embedded logic hardware devices instead of CPUs, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. Also, in one or more embodiments (not shown in the figures), the network computer may include one or more hardware microcontrollers instead of CPUs. In one or more embodiments, the one or more microcontrollers may directly execute their own embedded logic to perform actions and access their own internal memory and their own external Input and Output Interfaces (e.g., hardware pins or wireless transceivers) to perform actions, such as System On a Chip (SOC), or the like.

Illustrative Logical System Architecture

Figure 4:
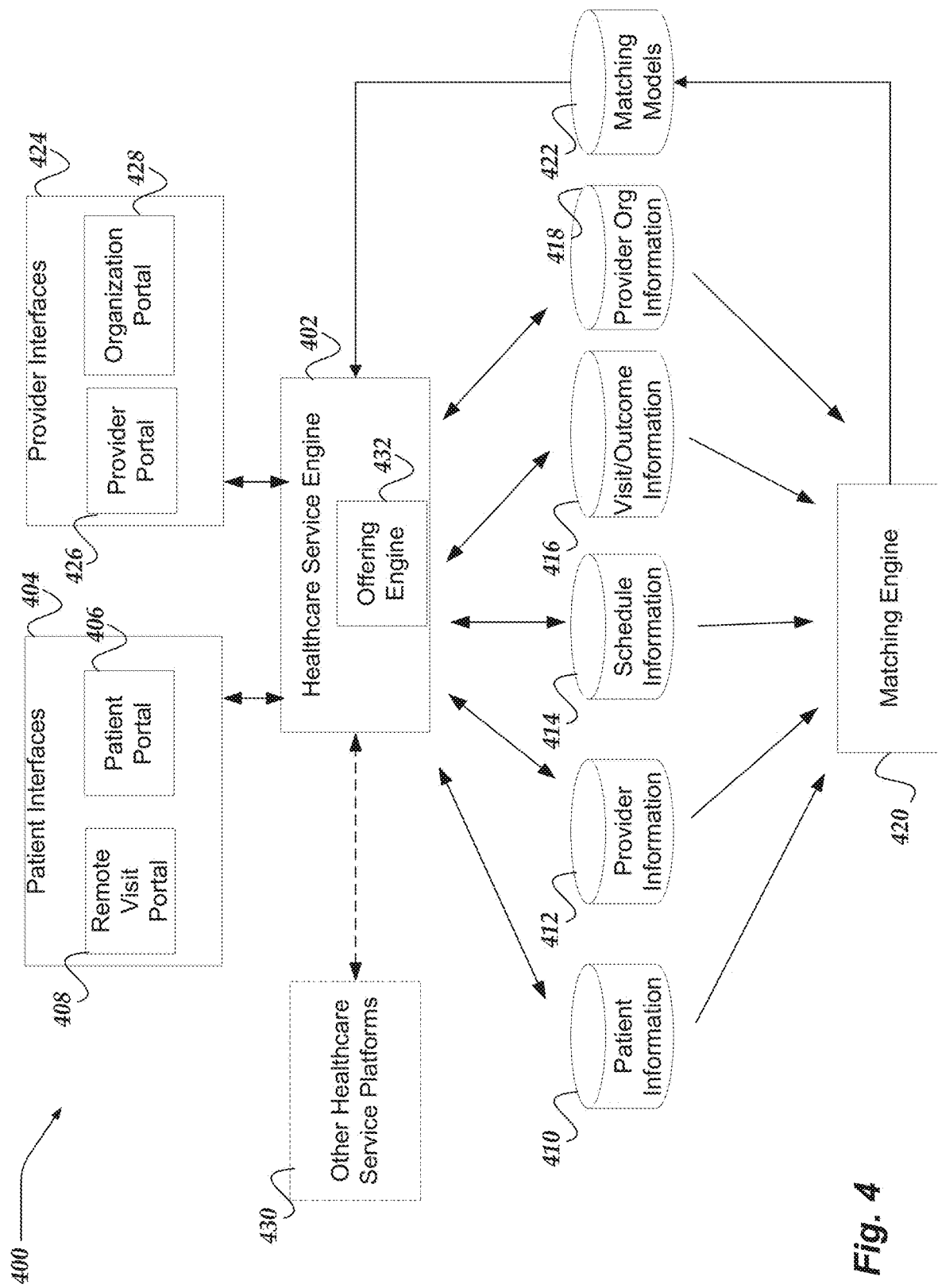
FIG. 4 illustrates a logical architecture of a system for healthcare service platform that may be configured to generate service offerings based on associated content and historical data in accordance with one or more of the various embodiments.

FIG. 4 illustrates a logical architecture of system 400 for healthcare service platform that may be configured to generate service offerings based on associated content and historical data in accordance with one or more of the various embodiments. In one or more of the various embodiments, healthcare service platforms may be comprised of various elements, including, healthcare service engine 402, patient interfaces 404, remote visit portal 406, patient portal 408, patient information data store 410, provider information data store 410, schedule information data store 410, visit/outcome information data store 410, matching engine(s) 420, learned models data store 422, provider interfaces 424, provider portal 426, provider organization portal 428, other healthcare service platforms 430, offering engine 432, or the like.

Also, in some cases, for some embodiments, one or more healthcare service platforms may be configured to communicate/coordinate with one or more other healthcare service platforms, such as, other healthcare service platforms 424.

In one or more of the various embodiments, healthcare service engines, such as, healthcare service engine 402 may be arranged to process various requests from patients, providers, or provider organizations. In some embodiments, healthcare service engines may be arranged to process requests from one or more authorized third-party services, such as insurance providers, or the like. In some embodiments, healthcare service engines may be arranged to exchange information with other third-party services, such as, EHR systems, hospital management systems, billing services, or the like. In some embodiments, healthcare service engines may be arranged to enable patients to schedule visits with providers. Also, in some embodiments, healthcare service engines may be arranged to enable provider organizations to manage patients, providers, visits, or the like.

In one or more of the various embodiments, healthcare service platforms may be arranged to provide one or more patient interfaces, such as patient interfaces 404. In some embodiments, patient interfaces 404 represent one or more user interfaces or APIs that may employed by patients or services on behalf of patients to access healthcare services.

In some embodiments, patient interfaces may provide one or more patient portals, such as, patient portal 406. In one or more of the various embodiments, patient portals may be arranged to provide interactive reports, user interfaces, or the like, that enable patients to view or interact with their healthcare providers. In some embodiments, patient portals may be arranged to enable patients to review upcoming appointments, past appointments, request new appointments, or the like. Further, in some embodiments, patient portals may be arranged to enable patients to view some or all of their electronic health records (EHRs). In some embodiments, patient portals may be communicatively coupled with healthcare service engine 402 using one or more networks. Accordingly, in some embodiments, healthcare service engines may be arranged to provide the information that may be presented in the patient portal.

In one or more of the various embodiments, provider organizations may be enabled to customize user interfaces or reports that may be provided to their patients, including the care settings, providers and modalities that may be best for them based upon their interests, motivations and clinical needs. In some embodiments, portions of patient portals may be customized by patients. In some embodiments, healthcare service engines may be arranged to determine the user interfaces or reports that may be presented or accessed from patient portals based on rules, instructions, or the like, provided via configuration information to account for local circumstances or local requirements.

In one or more of the various embodiments, patient portals may be comprised of one or more mobile applications, desktop applications, web-based applications, or the like.

In one or more of the various embodiments, patient interfaces 404 may be arranged to provide remote visit portals, such as, remote visit portal 408. In one or more of the various embodiments, remote visit portals may be arranged to enable patients and providers to conduct scheduled visits using video conferencing, teleconferencing, or the like, or combination thereof. In some embodiments, remote visit portals may be arranged to include virtual waiting rooms that enable providers/provider organizations to request or collect pertinent information from patients that may be queued for scheduled visits.

In some embodiments, remote visit portals may be arranged to provide user interfaces for chat services that enable incoming patients to describe symptoms, submit questions, or the like. In some embodiments, healthcare service engines may be arranged to provide both computer automated chat systems (e.g., chat bots) as well as human monitored chat services.

In one or more of the various embodiments, healthcare service engines, such as, healthcare service engine 402 may be arranged to employ one or more data stores to collect or organize some or all of the information associated with providing healthcare services. In some embodiments, the one or more data stores may include data stores, such as, patient information data store 410, provider information data store 412, schedule information data store 414, visit/outcome information data store 416, provider organization information data store 418, or the like. Accordingly, in some embodiments, healthcare service engines may be enabled to store various information associated patients, providers, or provider organizations, such as, vital information, administrative information, billing/payment information, insurance information, visit history, scheduled appointments, medical history, financial information, performance tracking information, resource utilization information, services offered, department/specialty organization, or the like. In some embodiments, healthcare service engines may be arranged to provide EHRs for patients.

Alternatively, in some embodiments, healthcare service engines may integrate with one or more authorized EHR providers rather than acting as a repository for EHRs. Accordingly, in some embodiments, healthcare service engines may be arranged to exchange some information with authorized EHRs rather than storing EHR information in local data stores.

Likewise, in some embodiments, healthcare service engines may be enabled to store various information associated with providers, such as, availability information, utilization information, specialty information, training/education information, compensation information, visit outcome information, scheduled appointments, or the like.

Also, in one or more of the various embodiments, healthcare service platforms may include one or more matching engines, such as, matching engine 420, or the like. In some embodiments, matching engines may be arranged to employ information collected by healthcare service engines for training or generating one or more machine learning models, including one or more predictive models, one or more classification models, or the like. In some embodiments, matching engine 420 may be enabled to access the various data stores to train one or more matching models that may be stored in matching model data stores, such as, matching data store 422.

In one or more of the various embodiments, healthcare service platforms may be arranged to include matching engines that may apply different machine learning techniques to train models for a variety of applications. Accordingly, in some embodiments, healthcare service engines or matching engines may be arranged to employ configuration information to determine which actions to perform for machine learning. For example, matching engine 420 may be arranged to dynamically load or instantiate one or more machine learning trainers based on configuration information to account for local circumstances or local requirements. In some embodiments, one or more machine learning engines may be hosted in computing environments that may be separate from healthcare service engines. For example, in some embodiments, healthcare service platforms may be arranged to employ one or more off-site machine learning compute clusters hosted in a cloud computing environment to train matching models for the healthcare service platform.

Also, in some embodiments, healthcare service engines may be arranged to provide one or more provider interfaces, such as, provider interfaces 424 that enable providers or provider organizations (e.g., administrative personnel, or the like) to engage with the healthcare service engines. Accordingly, in some embodiments, provider interfaces may include one or more provider portals, such as, provider portal 426 that may enable providers to review practice related information, such as, upcoming appointments, or the like. In some embodiments, provider portals may be arranged to enable providers to communicate with patients (e.g., secure messaging), review past visits, accept/decline visit requests, approve/disapprove treatment requests, approve/disapprove prescription requests, or the like.

Also, in one or more of the various embodiments, provider interfaces may be arranged to provide provider organization portals that enable provider organization representatives to review or interact with practice related information. In some embodiments, provider organization portals may include some information or user interfaces that may be similar to provider portals, except rather than being limited to one provider, provider portals may include information (e.g., patient queues, schedules, visit history, or the like) associated with more than one or more provider. For example, in some embodiments, provider portals may include scheduling/visit information for an entire healthcare network, hospital, clinic, specialty group, or the like.

In one or more of the various embodiments, healthcare service engines may be arranged to restrict access to the information included in provider portal based on the organizational structure of the provider organizations. Accordingly, in some embodiments, one or more users of a provider portal may have access to different information. For example, in some embodiments, a healthcare service engine may provide a provider portal scoped to multiple clinic/hospital locations in a healthcare network while other provider portals may be scoped to one location or one group within the same healthcare network.

Further, in some embodiments, healthcare service engines may be arranged to integrate with one or more other healthcare service platforms, such as, other healthcare service platforms 430. In some embodiments, healthcare service engines may be arranged to rely on other healthcare service platforms to store some or all patient information, provider information, scheduling information, or the like. For example, healthcare service engines may be arranged to communicate with the other healthcare service platforms to access or update patient information.

Also, in some embodiments, healthcare service platforms may be arranged to include offering engines such as offering engine 432. In some embodiments, offering engines may be included in healthcare service engines or arranged as a separate process or compute instance. In this example, for some embodiments, offering engine 432 is represented as being part of healthcare service engine 402.

In some embodiments, offering engines may be arranged to analyze or evaluate content such as articles, blog posts, web pages, audio podcasts, videos, scientific papers, or other digitized media to determine or generate offerings for various services (e.g., tele-visits, in-person appointments, or the like) that may be tailored to the user/patient consuming the content based on the subject matter of the content. In some embodiments, offering engines may be arranged to generate or present offering panels to users/patients. Offering engines are described in more detail below.

Figure 5:
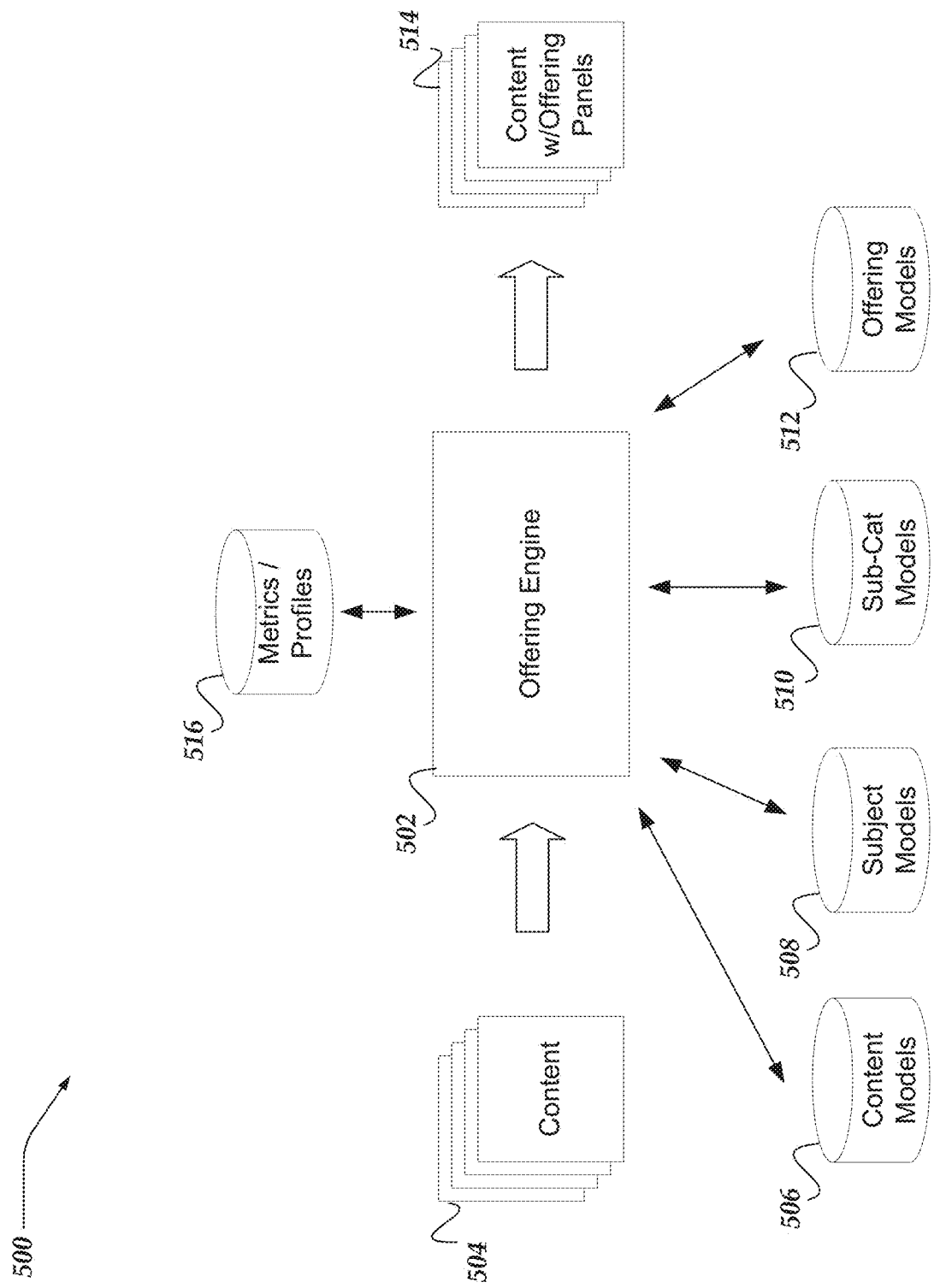
FIG. 5 illustrates a logical schematic of a system for generating service offerings based on associated content and historical data in accordance with one or more of the various embodiments.

FIG. 5 illustrates a logical schematic of system 500 for generating service offerings based on associated content and historical data in accordance with one or more of the various embodiments.

In one or more of the various embodiments, offering engines such as offering engine 502 may be arranged to evaluate or analyze content information or other relevant information to determine service offerings that may complement the content.

In some embodiments, offering engines may be arranged to be provided content such as content 504. In some embodiments, content may be provided from various sources including web pages, audio podcasts, videos, or other digitized media. In some embodiments, content may be provided in real-time as users are viewing or otherwise consuming the content. For example, in some embodiments, healthcare service platforms or other media servers may submit content to offering engines as users are accessing the content. Also, in some embodiments, content may be processed "off-line" absent an active user. Also, for example, in some embodiments, offering engines may be configured to automatically navigate web pages or file system directories to obtain content absent users actively consuming the content media.

Accordingly, in some embodiments, offering engine 502 may be arranged to employ one or more content models such as content models 506 to determine how to extract the content body from the media (e.g., web page, audio file, office document, or the like) that includes the content information. For example, in some embodiments, content included in a web page may include non-content related artifacts such as, advertising, styling, provider organization branding, or other non-content information. Accordingly, for example, in some embodiments, offering engines may be arranged to employ content models to extract the relevant content information from the content. Note, for brevity or clarity, herein the term content may be assumed to refer to the relevant content text absent styling, branding, or other non-information related formatting.

In some embodiments, if the content has been determined, offering engines may be arranged to employ one or more subject models to evaluate the content to infer or predict one or more subjects that are discussed or associated with the content. For example, in some embodiments, offering engines may be arranged to generate prompts that may be submitted to large language models, or the like, to determine the subjects of the content based on responses from the large language models. In some embodiments, subject models may include one or more heuristics, filters, NLP, or the like, rather than being limited to prompts or large language models.

In some embodiments, if one or more subjects for the content may be determined, offering engines may be arranged to employ one or more subject-category models, such as subject-category models 510 to map the subjects included in the content to one or more service categories, if any. In some embodiments, in some cases, several subjects determined from content may be associated with the same service category. Accordingly, in some embodiments, subject-category models may be arranged to infer or predict one or more relevant categories. Also, in some embodiments, subject-category models may determine that the subjects may be unrelated to service categories associated with provider organizations or providers. Further, in some embodiments, offering engines may be arranged to enable provider organizations or providers to configure one or more subjects or categories that may be excluded such that those subjects or categories may be excluded from the offering generation process.

In some embodiments, if the content may be determined to include subject matter that maps to a relevant service category, offering engines may be arranged to employ one or more offering models to generate offering profiles that include offering information. In some embodiments, offering information may include available appointment date/times, available providers, available locations, appointment types, or other information that may be relevant to enable a user to progress to requesting a service associated with the service category.

In one or more of the various embodiments, offering engines may be arranged to generate offering profiles that include user interface layout information, format information, or other styling information as well as concrete information associated with providing the offered, recommended, or referred service.

In one or more of the various embodiments, offering engines may have access to additional information about the user/patient. For example, in some embodiments, the user may be authenticated to a patient portal or other authorized application. Accordingly, in some embodiments, offering engines may be arranged to include patient information if generating offerings. For example, patient information may include patient preferences (e.g., time-of-day preferences, day-of-week preferences, or the like.) that may influence generated offerings. For example, if the patient is known to prefer tele-visits, offering engines may prioritize tele-visit appointments over in-person service offerings. In some embodiments, additional information may be included in offering profiles.

In some embodiments, if an offering may be determined, offering engines may be arranged to generate one or more offer user interfaces (e.g., offering panels) that may be included in or displayed with the content. In some embodiments, offering user interfaces may be offering panels that may be displayed in the same web page (or the like) where the content is hosted. Also, in some embodiments, offering user interfaces may include embedding one or more links, URLs, references, or the like, that enable the user access another screen or view that may be display the offering panels associated with the service offering. Also, similarly, in some embodiments, offering engines may be arranged to display a portion of the service offering information near the content, enabling the user to navigate to another user interface that displays more offering information, visit options, or the like.

Accordingly, in some embodiments, content panels such as content panels 514 may represent content that may be associated with offering user interface panels. In practice, content panels may be web pages, portions of web pages, or other static or interactive displays presented or displayed by one or more applications or communication services.

Further, in some embodiments, data stores, such as, metric/profiles 516 may be employed to store performance metrics, performance profiles, offering profiles, input records, or the like, that offering engine may be arranged to employ for evaluating or retraining offering models.

FIG. 6 illustrates a logical schematic of content panel 600 that includes service offerings based on associated content and historical data in accordance with one or more of the various embodiments. As mentioned above, in some embodiments, offering engines may be arranged to generate offering panels that may be intended for displaying or otherwise including with particular content.

In some embodiments, a content panel, such as content panel 600 may be arranged to include content, such as content 602. Accordingly, in some embodiments, offering engines may be arranged to evaluate or analyze content such as content 602 to determine or generate offering panel 604 based on the analysis of content 602.

In some embodiments, offering engines may employ offering models to generate offering profiles that may be used to generate one or more offering panels that may include various text, user interface controls, styling, formatting, or the like. In some embodiments, offering engines or particular offering models may be configured to employ one or more templates, user interface frameworks, or the like, for determining the appearance or placement of offering panels. Accordingly, in some embodiments, offering engines may be arranged to determine particular messaging, availability information, or the like, for a particular offering based on one or more of the subject of the content, patient/user information, provider information, provider organization information, provider preferences, provider organization preferences, patient/user preferences, or the like. For example, in some embodiments, an offering model trained for generating appointment offerings may generate offering profiles that include field values for provider name, provider location, appointment type, appointment availability, or the like, that may be included in offering panels. Thus, in some embodiments, if a patient/user may be consuming content, offering panels may offer services that may be related to one or more subjects included in the content. Further, in some embodiments, if patient information may be available (e.g., user is authenticated as a patient), some or all patient information may be included in offering profiles or otherwise employed to guide the generation of offering panels.

Figure 7:
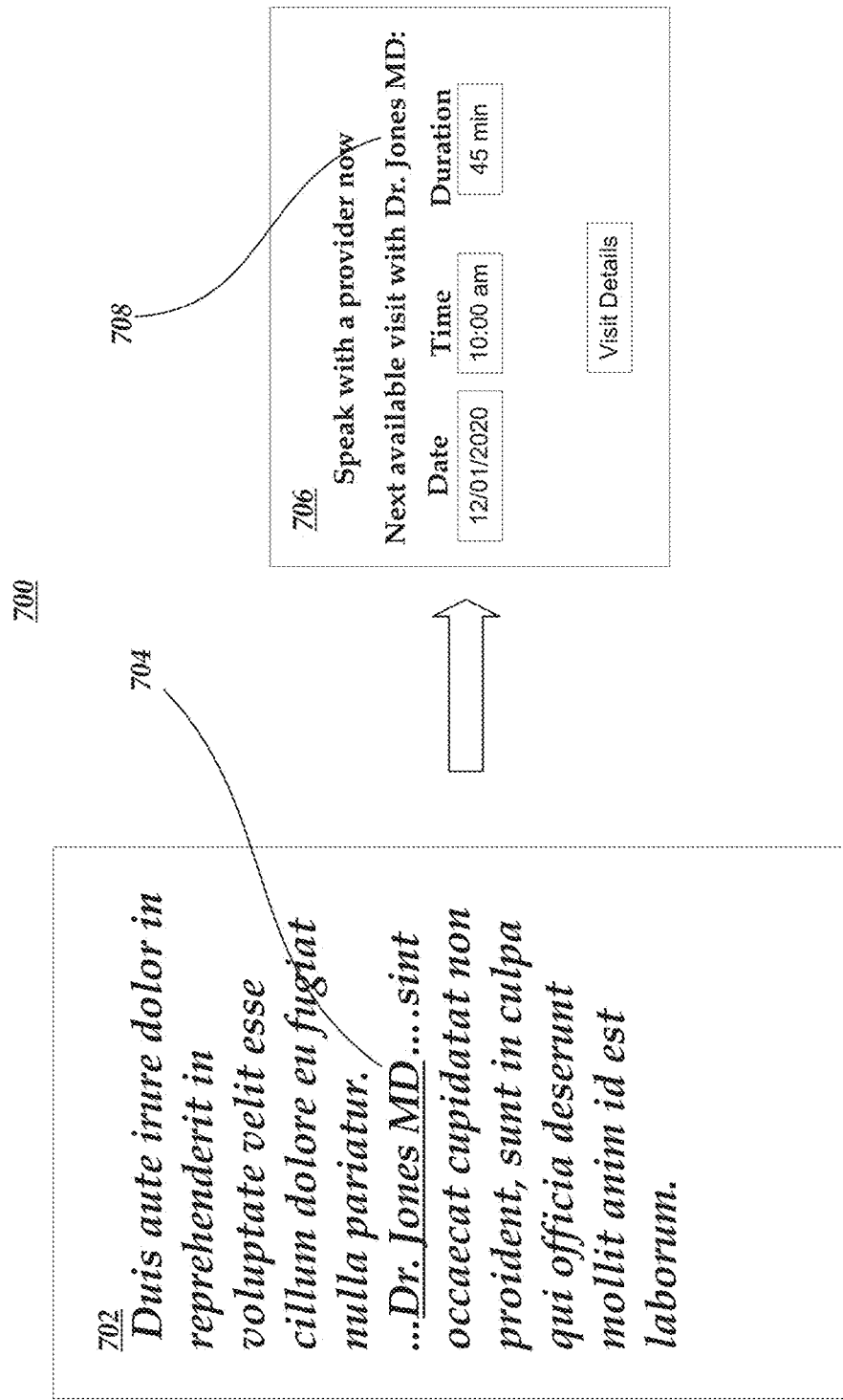
FIG. 7 illustrates a logical schematic of a system for generating service offerings based on associated content and historical data in accordance with one or more of the various embodiments.

FIG. 7 illustrates a logical schematic of system 700 for generating service offerings based on associated content and historical data in accordance with one or more of the various embodiments.

In some embodiments, offering engines may be arranged to modify content to include links, URLs, or other user interface elements that may reference offering panels rather including the offering panels alongside the content in the content panel.

Accordingly, offering engines may be arranged to determine one or more portions of the content that may be related to relevant offerings. In some embodiments, offering engines may be arranged to determine one or more keywords, provider names, disease/] ailment descriptions, symptom/feature narratives, or the like in the content that may be modified to include references to generated offering panels. In this example, for some embodiments, offering engines may convert a mention of a provider into links, such as link 704 may be included in content 702. Accordingly, in some embodiments, if a user activates the link, offering panel 706 may be displayed to the user. In this example, offering panel 706 is illustrated as including provider name 708 that includes the name of the provider that was associated with link 704.

In one or more of the various embodiments, offering engines may be arranged to generate offering panels that may be displayed in separate windows, pages, views, or the like. Also, in some embodiments, rather than using links that may be embedded in the content, offering engines may be arranged to provide user interface controls, such as, buttons, links, or the like that may be displayed separate from the content. For example, in some embodiments, offering engines may be configured to include a user interface button near the content rather than actually modifying the content to include a link or other user interface feature.

Figure 8:
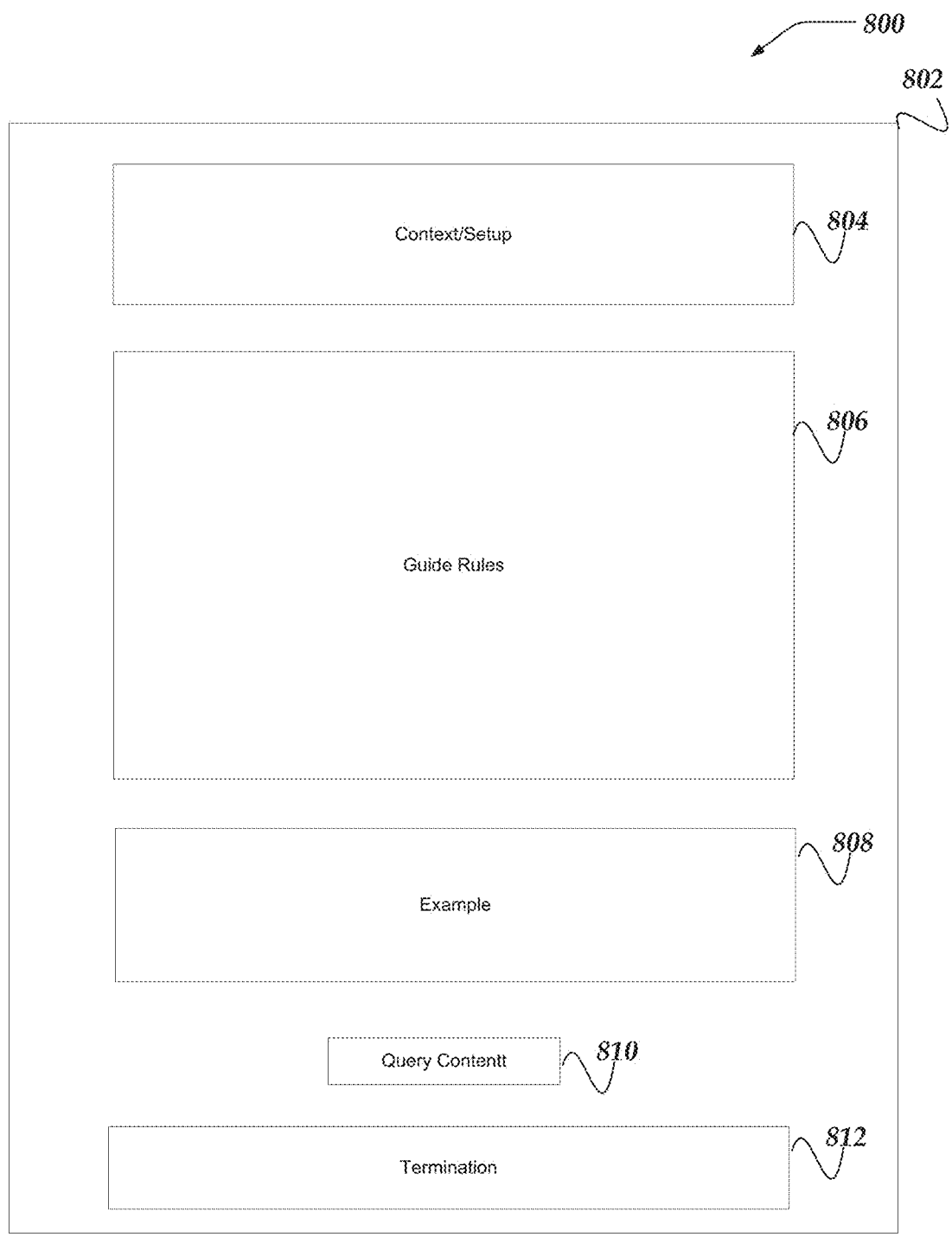
FIG. 8 illustrates a logical schematic of a prompt for generating service offerings based on associated content and historical data in accordance with one or more of the various embodiments.

FIG. 8 illustrates a logical schematic of prompt 800 for generating service offerings based on associated content and historical data in accordance with one or more of the various embodiments. As described above, in some embodiments, offering engines may be arranged to determine a prompt template from among one or more prompt templates. In some embodiments, if a prompt template may be determined and a query statement is provided, offering engines may be arranged to generate a prompt based on the prompt template and the query statement.

One of ordinary skill in the art will appreciate that the particular contents or text included in prompt templates may vary depending on various factors, including, the large language model (e.g., different types/version/brands of LLMs may require different prompt templates), format or content required for desired responses, offering preferences, or the like. In general prompt templates may be developed experimentally such that prompt templates produce prompts that may be used to real-time train large language models to produce responses that conform to the requirements of healthcare service platforms or offering engines. In some embodiments, prompt templates may be included in a prompt template repository or other data store. In some cases, employing prompts to train a more generalized language model to provide particular results that the language model may not explicitly be trained or tuned for may be referred to as zero-shot learning, few-shot learning, one-shot learning, or the like because the generalized language model (referred to herein as large language models) is trained by the prompts in real-time to produce the desired results. Accordingly, in some embodiments, large language models that consume prompts may perform transfer learning, or the like, to provide specific results, such as content subjects, subject-category matches, offering profiles, or the like.

Accordingly, in some embodiments, the particular contents of prompt templates or prompts may depend on the semantic understanding capabilities of the underlying large language model. Thus, in some cases, different large language models may require different prompt templates. Further, in some embodiments, different large language models may be engineered to address different target audiences, problem domains, or the like. Accordingly, in some embodiments, offering engines may be arranged to select among multiple large language models depending on the queries, response targets, transaction costs, latency, or the like.

In some embodiments, prompt templates may comprise a dataset container, such as, container 802 that may hold the contents (e.g., text or audio) for the prompt. Also, in some embodiments, prompt templates may be configured to include various sections, including, for example, context section 804, guide rule section 806, example section 808, query statement placeholder 810, termination section 812, or the like. In some cases, for some embodiments, prompt templates may omit one or more sections. Likewise, in some embodiments, prompt templates may include one or more other sections. Further, in some cases, prompt templates may arrange the various sections in a different order than shown here. Thus, in some embodiments, offering engines may be arranged to employ different prompt templates for different problems or different large language models as needed.

In one or more of the various embodiments, prompt containers may be variables, parameters, objects, data structures, or the like, that enable the prompts to be passed to a large language model. In some cases, for some embodiments, a prompt container may be a buffer of text characters that form a string collection that may be included in the prompts. Likewise, for example, a prompt container may be an object or class instance designed for handling the types of content (e.g., string, audio, or the like) included in a particular prompt.

In one or more of the various embodiments, context sections such as context section 804 may be portions of a prompt template that inject statements that establish a working context that may aid in the training of the large language model to generate offering profiles. For example, in some embodiments, context sections may be employed to declare one or more features or characteristics of a content, patients, provider organizations, or the like. Accordingly, in some embodiments, large language models may incorporate this context information as part of the generative process that produces the content subject inference or offering profiles.

In one or more of the various embodiments, guide rule sections such as guide rule section 806 may be portions of a prompt template that inject one or more statements that may be selected to provide additional guidance or direction for training the large language model to generate the desired responses (e.g., subject inference or offering profiles). For example, in some embodiments, guide rules may include statements that declare rules for omitting certain types of punctuation, omitting in-depth explanation text from offering profiles, directives to specifically or particularly take actions if certain words or text forms are encountered while generating offering information, or the like.

In one or more of the various embodiments, example sections such as example section 808 may be a portion of a prompt template that include one or more examples of the offering information or subject inferences that may correspond to the example query statement. In some embodiments, if needed, the example information may guide the training of the large language model to generate offering information that conforms to the requirements of the healthcare service platforms or supported organizations.

In one or more of the various embodiments, query statement placeholders such as query statement placeholder 810 may be specialized tokens, markers, mark-up, or the like, that indicate where in the prompt template that the actual query statement should be embedded in the prompt. In some embodiments, query statements may include input records (for offering models), subjects (for subject-category models), or the like.

In one or more of the various embodiments, termination sections such as termination section 812 may be a portion of a prompt template that includes additional context information or guide rules that may be required to "close" prompts or end real-time training events. For example, for some embodiments, termination sections may include a text statement indicating that the large language model should end the text generation session, or the like.

Further, in some embodiments, offering engines may be arranged to employ one or more pre-made prompt engineering frameworks that support key words, data definitions languages, formatting, or the like, that enable parameterized prompt generation such that offering engines may be arranged to provide particular parameters or inputs that enable the prompt engineering framework to generate the actual prompts that may be provided to LLMs.

Figure 9:
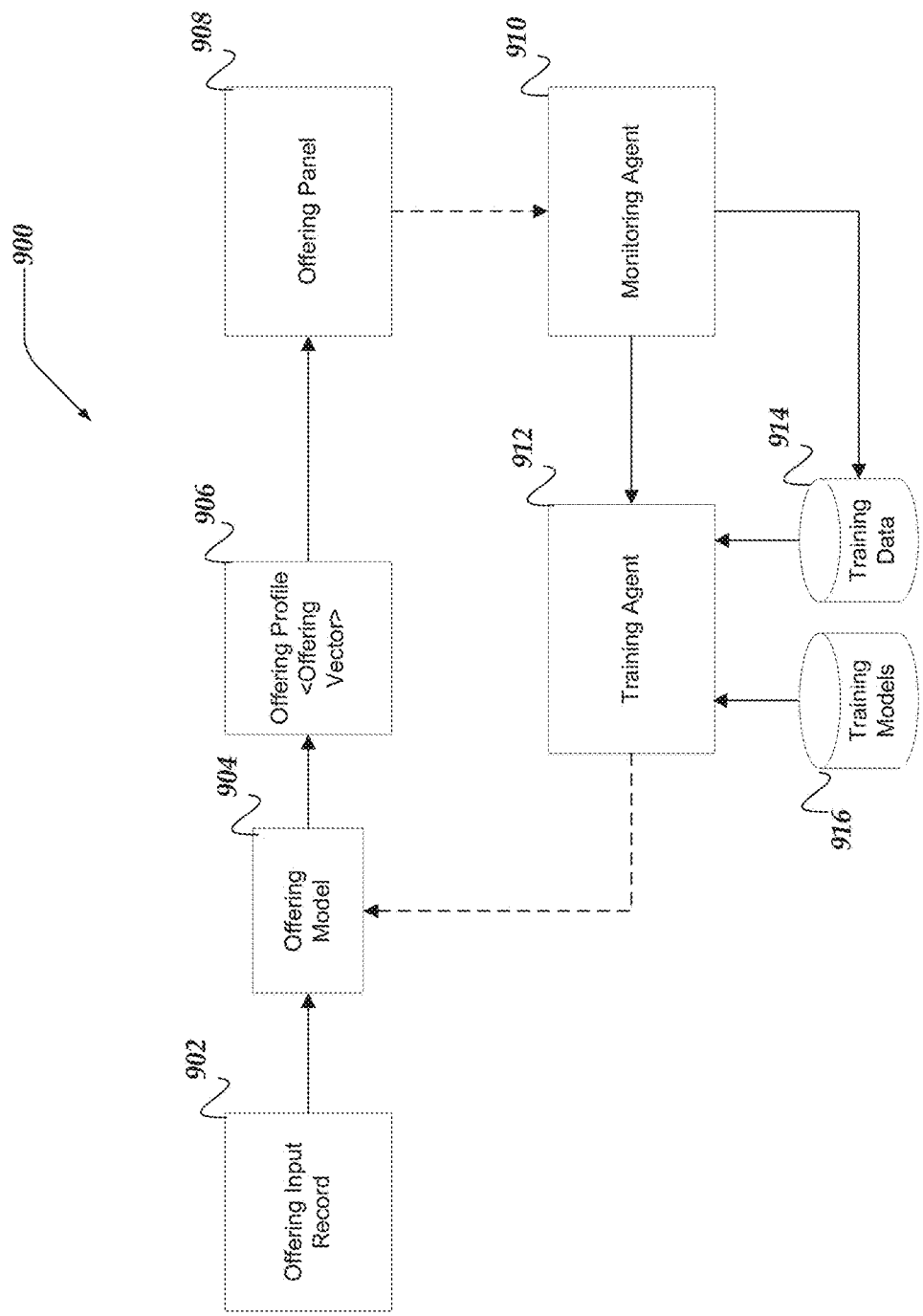
FIG. 9 illustrates a logical schematic of a system for generating service offerings based on associated content and historical data in accordance with one or more of the various embodiments.

FIG. 9 illustrates a logical schematic of system 900 for generating service offerings based on associated content and historical data in accordance with one or more of the various embodiments. In some embodiments, offering engines that employ various models as described herein for ultimately generating offering panels may be arranged to automatically self-monitor the quality of offerings based on one or more metrics. In some embodiments, some or all such metrics may be based on observing how users or patients interact with the offering panels. Accordingly, in some embodiments, offering panels that may be less effective than desired or expected may be identified based on one or more metrics falling below a threshold value. Accordingly, in some embodiments, offering engines may be arranged to infer that the offering models associated with the sub-standard offering panels may require re-training or replacement.

In some embodiments, offering models that were initially performing to standard may degrade overtime as external conditions may deviate or skew away from the initial conditions used for configuring or training the offering models. For example, in some embodiments, patient population of an organization may change, service offering of provider organizations may change, access to or availability of particular healthcare providers may change, or the like. For example, in some embodiments, a healthcare provider organization may change which insurance carriers are accepted or preferred resulting in significant changes in patient population characteristics or patient behavior. Likewise, in some embodiments, particular providers with particular specialties may leave (or join) a provider organization resulting in significant changes to service offerings or patient preferences (e.g., patients may follow favorite providers to different organizations).

Accordingly, in some embodiments, offering engines may be arranged to provide offering input records, such as offering input record 902 to an offering model, such as offering model 904. In some embodiments, offering engines may be arranged to employ responses from offering model 904 to generate an offering profile such as offering profile 906 which may be employed to generate offering panels such as offering panel 908.

In one or more of the various embodiments, offering input record 902 may be considered a vector of input values that may be provided to offering models. In some embodiments, such input records may include data such as, service category, patient information, user information, content information, or the like. In some cases, the input record (e.g., patient information) may be limited if the user is not known the healthcare service platform. Thus, in some embodiments, input records may include variable information depending on the information (or user status) that may be available at the time the offering panel may being generated or selected.

In some embodiments, offering profiles may be considered to be data structure representations of offering panel features or characteristics that may be employed to determine one or more of text, fields, layouts, positioning, input controls, or the like, for defining how offering panels may be generated or presented. Accordingly, in some embodiments, offering profiles may be employed to track the features or characteristics of each generated offering panel. In some embodiments, offering profiles may include more fields or features than are actually used or visible in the offering panels. For example, for some embodiments, one or more offering profiles may include meta-data such as offering model version, timestamps, content/publication identifiers, organization identifiers, or the like. Also, in some embodiments, one or more fields or values from input records may be passed through to offering panels.

Also, in some embodiments, offering model responses may indicate some or all of the particular features to include in offering panels. For example, in some embodiments, for some categories or type of services the provider name may be omitted from offering panels. Likewise, in some embodiments, some cases, offering model responses may indicate that the offering panel should be accessed via a link rather than being positioned or displayed near the content. Accordingly, in some embodiments, offering profiles may include information that offering engines may decode to determine which information to include or display in offering panels as well as information which may be employed guide how the offering panel may be displayed or styled.

Accordingly, in some embodiments, offering engines may be arranged to develop a record of the offering profiles or offering panels used for generating service offerings based on associated content and historical data.

In some embodiments, offering engines may be arranged to include one or more monitoring agents such as monitoring agent 910 for passively or actively collecting metrics associated with deployed offering panels. For example, in some embodiments, monitoring agents may be arranged to track how users or patients interact with particular offering panels. Accordingly, in some embodiments, these metrics may be employed to evaluate the quality of efficacy of particular offering panels. Thus, in some embodiments, if one or more metrics fall below a configured threshold value, the associated offering model may be flagged or otherwise indicated as being deficient or selected for reevaluation.

In some embodiments, offering engines may be arranged to automatically or passively collect one or more metrics associated with patient interactions with offering panels, including click-thru counts, scheduled visits, completed visits, or the like. Thus, in some embodiments, offering engines may be arranged to evaluate efficacy of offering panels based on how or how often users/patients may interact with offering panels.

In some embodiments, offering engines may be arranged to provide one or more user interfaces that enable users, patients, providers, or administrators to submit evaluations regarding the efficacy of offering panels. For example, automated patient surveys may include questions related to the offering panels. Likewise, in some embodiments, providers or provider organization staff may be provided automated surveys to collect information that may be used for determining the efficacy or quality of offering panels.

Further, in some embodiments, offering engines (e.g., monitoring agents) may be arranged to sample or otherwise store metrics/offering profile information in a data store such as training data 914 for use in subsequent model training or model development. Accordingly, in some embodiments, offering engines may be arranged to develop a comprehensive record or how particular offering panels generated based on particular offering models (or offering model versions) may perform relative to other offering panels generated from other offering models. Likewise, in some embodiments, offering engines may track input record vectors and offering profiles to enable subsequent review or evaluation of model performance.

In one or more of the various embodiments, offering engines may be arranged to include training agents such as training agent 912 for retraining or evaluating offering models that have been indicated by monitoring agents. In some embodiments, training agents may be arranged to employ one or more training models such as training models 916 or training data 914 for retraining or evaluating indicated offering models. In some embodiments, training models may include machine learning classifiers, heuristics, filters, pattern matching, or the like that may be employed to evaluate or train offering models. In some embodiments, training models may include one or more exemplar offering models that may be employed to evaluate if indicated offering models deviate from a particular performance standard. Accordingly, in some embodiments, offering engines may be arranged to compare offering profiles or offering panels generated based on if the indicated offering models (e.g., models selected for retraining) with offering profiles or offering panels generated by the exemplar models. Likewise, in some embodiments, training models may be configured to compare offering panels generated by other in-production offering models with offering panels generated by indicated offering models to confirm if indicated offering models may be uniquely deficient.

Further, in some embodiments, offering engines may be arranged to employ training agents and training data to generate new offering models that may replace the indicated models. Also, in some embodiments, if the offering models may include or use prompts with large language models, training agents may be configured to experiment with using different prompts, different large language models, or the like. Further, in some embodiments, if the offering models may include conventional neural networks, training agents may be configured to employ input records, offering profiles, metrics, or the like, sampled/collected from other live offering models to retrain or replace offering models. Also, in some embodiments, training data 914 may include a curated set of input records, offering profiles, or the like, for training or retraining offering models.

Figure 10:
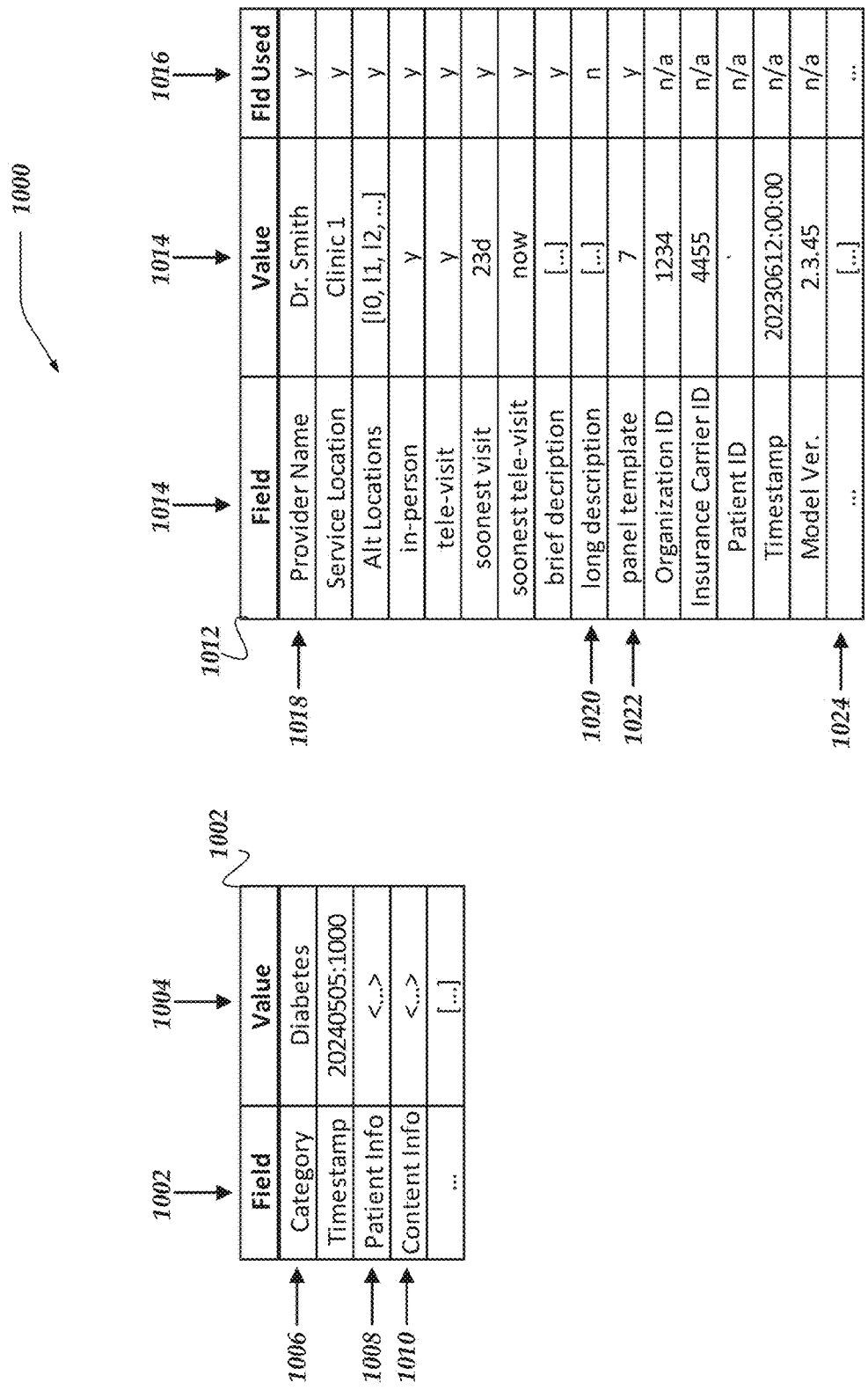
FIG. 10 illustrates logical schematics for a system for generating service offerings based on associated content and historical data in accordance with one or more of the various embodiments.

FIG. 10 illustrates logical schematics for system 1000 for generating service offerings based on associated content and historical data in accordance with one or more of the various embodiments.

As described above, in some embodiments, offering engines may be arranged to generate input records that may be provided to offering models to generate offering profiles that may be employed for generating offering panels.

In some embodiments, input records, such as input record 1002 may have one or more columns such as column 1002 for representing field name or column 1004 for storing field values. Accordingly, in some embodiments, input record 1002 may include various fields for storing input records. In some embodiments, input data fields may include field 1006 for storing the service category determined to be associated with the content. In some cases, for some embodiments, field values may be vectors or lists. For example, in some embodiments, field 1008 may be considered to include a vector or list of patient information where patient information may include patient demographic information, insurance status, last-visit, assigned provider, assigned clinic, or the like. In some cases, the patient information may depend on if the healthcare service platform knows if the user is a patient. For example, a user that is not logged in or otherwise identifiable may be not be known to be a patient. Accordingly, in this example, some or all patient information may be omitted. Similarly, in some embodiments, there may be one or more fields such as field 1010 for representing information about the content where the offering panel may be directed. For example, in some embodiments, content information may indicate the source of the content, the type of content, or the like.

Further, as described above, offering engines may employ offering models to generate offering profiles that may be used to generate offering panels. As described above, offering profiles may be tables or vectors that include one or more fields representing features or characteristics for generating offering panels. Accordingly, in this example, offering profiles such as offering profile 1012 may include one or more columns such as column 1014 for representing field names, column 1016 for storing field values, column 1018 for indicating if the field should be included in offering panels, or the like. The particular fields may vary depending on the response from offering models. In this example, for some embodiments, offering profile 1012 includes field 1018 for identifying a provider name. Note, in this example, the provider name is indicated (by column 1016) as being included in the offering panel. In contrast, in this example, field 1020, representing a long description is indicated as being omitted from display in corresponding the offering panels.

Note, for brevity and clarity input record 1002 and offering profile 1012 are represented here using tables. One of ordinary skill in the art will appreciate that in practice other data structures, such as, vectors, arrays, structures, objects, or the like, may be employed to represent this type of information without departing from the scope of the innovations disclosed herein.

Further, in this example, field 1024 represents how offering profiles or input data may include more or fewer fields depending on the type of information that may be available to offering engine or how the offering models, or the like, may be configured. For example, in some embodiments, rather than include field 1022 indicating a user interface template, offering profiles may be configured to include some or all styling information directly in the offering profile rather than referencing a template that may include the styling information.

Generalized Operations

FIGS. 11-16 represent generalized operations for generating service offerings based on associated content and historical data in accordance with one or more of the various embodiments. In one or more of the various embodiments, processes 1100, 1200, 1300 1400, 1500, and 1600 described in conjunction with FIGS. 11-16 may be implemented by or executed by one or more processors on a single network computer, such as network computer 300 of FIG. 3. In other embodiments, these processes, or portions thereof, may be implemented by or executed on a plurality of network computers, such as network computer 300 of FIG. 3. In yet other embodiments, these processes, or portions thereof, may be implemented by or executed on one or more virtualized computers, such as, those in a cloud-based or containerized environment. However, embodiments are not so limited and various combinations of network computers, client computers, or the like may be utilized. Further, in one or more of the various embodiments, the processes described in conjunction with FIGS. 11-16 may be used for healthcare service platforms in accordance with at least one of the various embodiments or architectures such as those described in conjunction with FIGS. 4-10. Further, in one or more of the various embodiments, some or all of the actions performed by processes 1100, 1200, 1300 1400, 1500, and 1600 may be executed in part by healthcare service engine 322, offering engine 324, or the like, running on one or more processors of one or more network computers.

Figure 11:
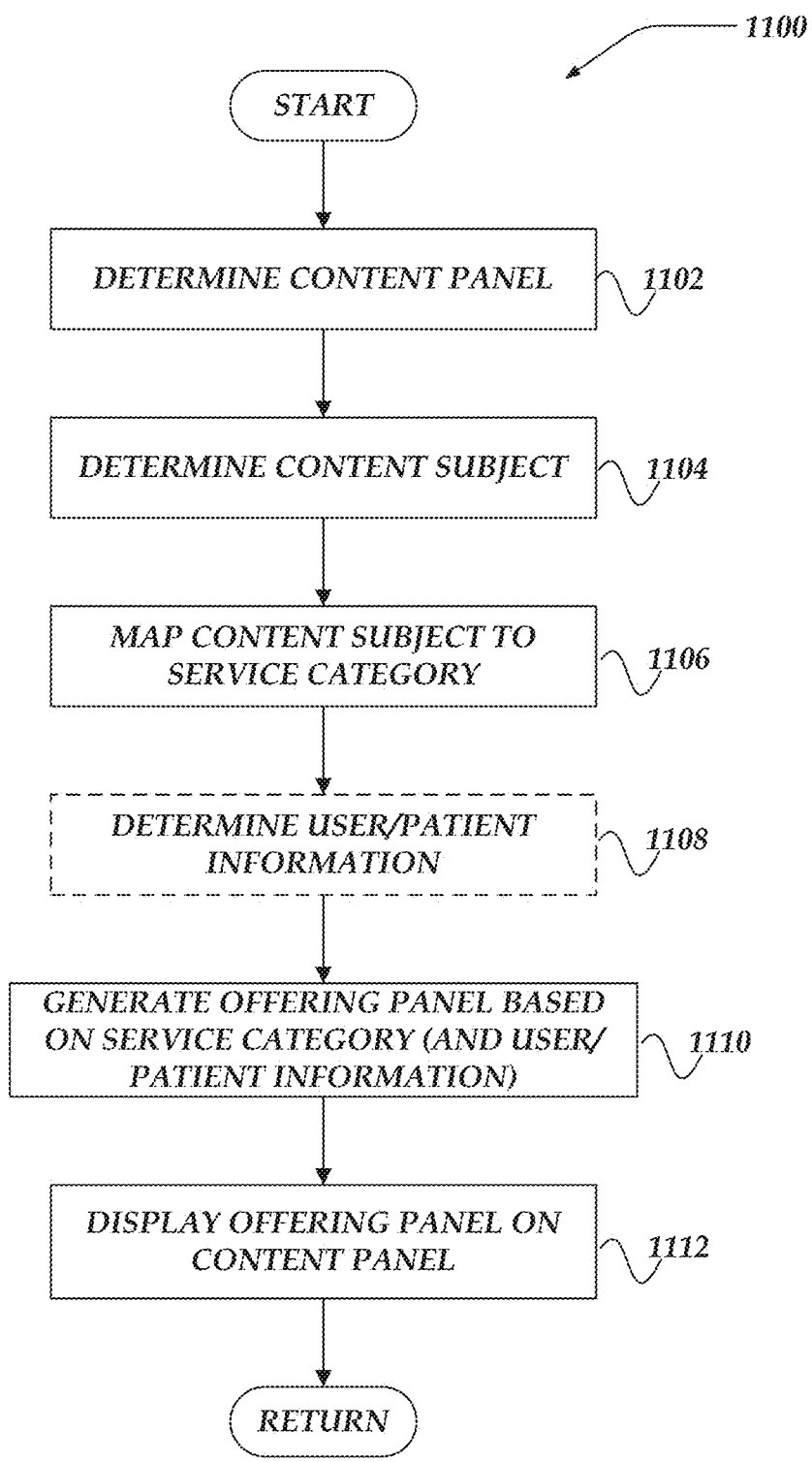
FIG. 11 illustrates an overview flowchart of a process for generating service offerings based on associated content and historical data in accordance with one or more of the various embodiments.

FIG. 11 illustrates an overview flowchart of process 1100 for generating service offerings based on associated content and historical data in accordance with one or more of the various embodiments. After a start block, at block 1102, in one or more of the various embodiments, offering engines may be arranged to determine a content panel or content container. In some embodiments, offering engines may be directed to scan or otherwise "read" content. In some embodiments, content may be included in content panels or content containers. In some embodiments, content panels may be considered the web pages, application views, or the like, that includes articles, blog posts, videos, audio, or the like.

In some embodiments, offering engines may be arranged to extract the content body from the content panels. In some embodiments, offering engines may be provided content directly absent the enclosing content panel. For example, in some embodiments, content services or content sites may employ content/document management systems that enable content to be accessed separately from the enclosing content panels. Also, in some embodiments, offering engines may be arranged to employ content scrapers, or the like, the may interpret content panels such as web pages to extract the content of interest while excluding some of styling information, format markup, sidebars, annotations, advertisements, branding, or the like.

At block 1104, in one or more of the various embodiments, offering engines may be arranged to determine the subject of the content. In some embodiments, offering engines may be arranged to employ one or more subject models to determine one or more subjects based on the content. In some embodiments, offering engines may be arranged to employ conventional NLP models or prompts and large language models to infer or predict one or more subjects that may be addressed in the content.

In some embodiments, content may be determined to include more than one subject. In some embodiments, offering engines may be arranged to rank or characterize subjects as major or minor subjects based on responses from subject models.

In some embodiments, subjects in this context may be considered to be one or more words that describe the general substance or subject matter than the content may be generally directed towards.

At block 1106, in one or more of the various embodiments, offering engines may be arranged to map the subject of the content to a service category. In some embodiments, subject models may often be configured to report subjects of content using words or language taken from the content. Accordingly, in some embodiments, offering engines may be arranged to employ one or more subject-category models that map the subject(s) to one or more service categories. In some embodiments, several subjects (or different subject representations) may be mapped to the same service category. In some embodiments, subject-category models may be configured include a confidence score with respect to the subject category mapping. In some cases, such as broadly defined subjects, subjects of a content may map to more than one service category.

In some embodiments, offering engines may be arranged to employ ontologies or dictionaries that may reflect how a particular healthcare organization or provider organize or describe their offered services. Also, in some embodiments, offering engines may be configured employ standardized ontologies provided by (or authorized by) regulatory agencies, insurance carriers, umbrella organizations, professional or practice specialty associations, or the like.

In some embodiments, subject-category models may be configured to employ NLP, heuristics machine learning, large language models, or the like, or combination thereof to determine the relevant service categories based on the one or more subjects of the content.

At block 1108, in one or more of the various embodiments, optionally, offering engines may be arranged to determine user/patient information associated with the viewing of the content. In some embodiments, content may be hosted on services (e.g., web sites, applications, or the like)

associated with the healthcare provider. Accordingly, in some embodiments, in some cases, the user may be a patient that has been authenticated (e.g., logged in) with the healthcare service platform. Alternatively, in some embodiments, users may be more or less anonymous.

Accordingly, in some embodiments, if the user may be an authenticated as a patient, offering engines may determine patient information for the user from the healthcare service platform. For example, offering engine may be arranged to collect patient demographic information, recent visit information, insurance information, other patient preferences, or the like, from the healthcare service platform.

Note, this block is indicated as being optional because in some cases for some embodiments user/patient information may be unavailable. Also, in some embodiments, offering engines may be arranged to enable healthcare providers or patients to configure privacy preferences that may determine which patient information may be made available to offering engines.

At block 1110, in one or more of the various embodiments, offering engines may be arranged to generate one or more offering panels associated with the service category or user/patient information. In some embodiments, offering engines may be arranged to generate input records based on the service category, patient information, organization preferences, content information, or the like. In some embodiments, input records may be organized using data structures that conform to the requirement of downstream offering models or other data processing. For example, in some embodiments, input records may be arranged into a vector of field values that may be submitted to an offering model.

Accordingly, in some embodiments, offering engines may be arranged to organize responses from offering models into offering profiles that may data structures that include the fields/values for defining the contents, appearance, or other styling for generating offering panels.

At block 1112, in one or more of the various embodiments, offering engines may be arranged to generate or display the offering panels in the content panel. In some embodiments, offering panels may be displayed alongside content or made accessible via links, user interface controls (e.g., buttons) or other references that may be shown in the content panel that hosts the content. In some embodiments, offering engines may be arranged to generate offering panels in real-time as users browse content panels. Also, in some embodiments, offering engines may be configured pre-process content panels to generate some or all offering panels in advance of users browsing them.

In some embodiments, offering engines may be arranged to record some or all input records and resulting offering profiles to enable retrospective evaluation of the offering panel generation. For example, in some embodiments, offering engines may be arranged to monitor user interactions with offering panels to collect performance metrics that may be associated with input records, offering profiles records, or offering panels to enable analytical evaluation of the offering panels.

Next, in one or more of the various embodiments, control may be returned to a calling process.

Figure 12:
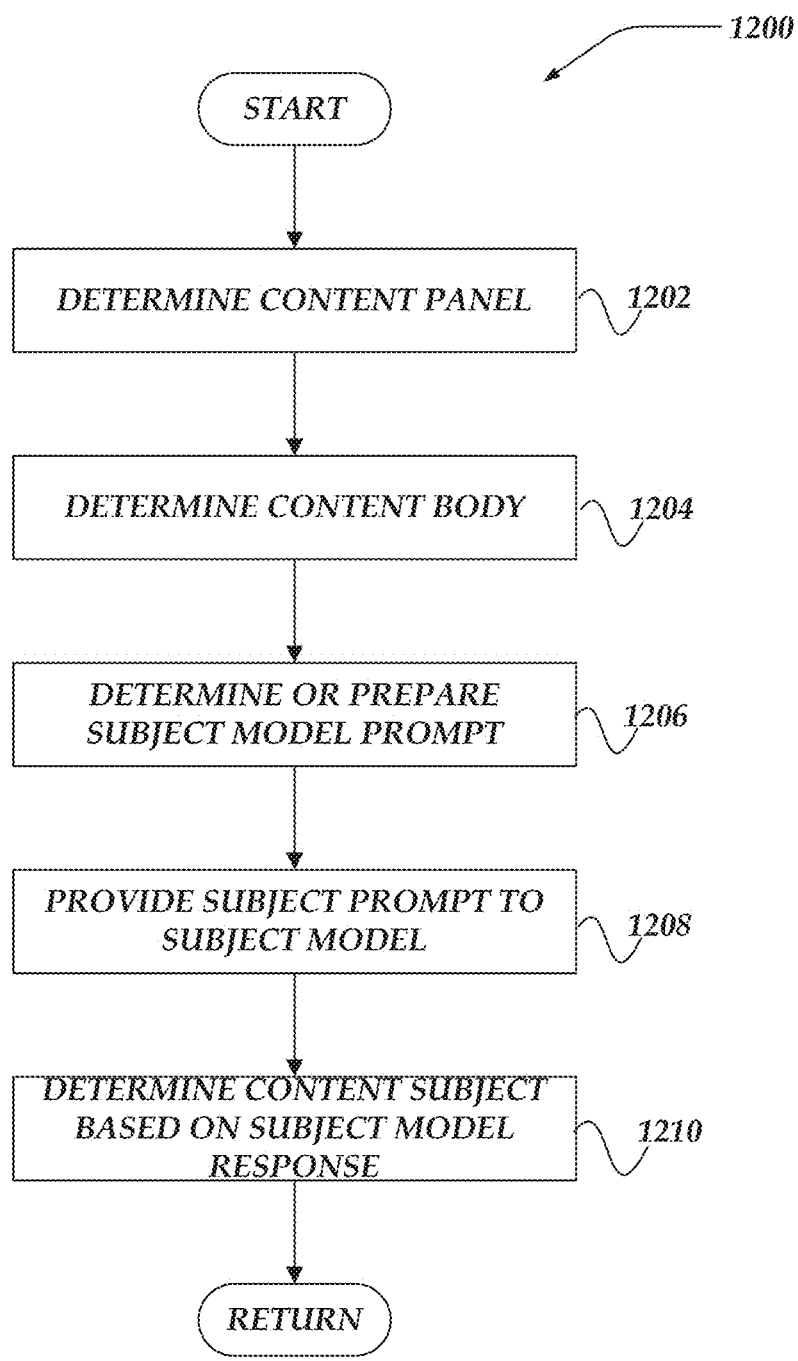
FIG. 12 illustrates a flowchart of a process for generating service offerings based on associated content and historical data in accordance with one or more of the various embodiments.

FIG. 12 illustrates a flowchart of process 1200 for generating service offerings based on associated content and historical data in accordance with one or more of the various embodiments. After a start block, at block 1202, in one or more of the various embodiments, offering engines may be arranged to determine a content panel or content container. In some embodiments, content that may be ingested by offering engines may be provided from web sites, applications, blog hosting sites, or the like. In some cases, users may be browsing content panels (e.g., web pages) hosted or associated with a healthcare provider or healthcare organization. In some embodiments, the content panels may be provided by third-party sites or organizations such that they agree to host or enable access to offering panels.

Accordingly, in some embodiments, the server or service that provided the content panel to users may be configured to provide content panels to offering engines. In some embodiments, offering engines may be arranged to provide one or more APIs or interfaces that enable content servers/providers to submit content panels to offering engines.

In some embodiments, offering engines may be arranged to process content panels off-line rather than in real-time as users are browsing.

At block 1204, in one or more of the various embodiments, offering engines may be arranged to determine the content body from the content panel. In some embodiments, in some cases, content may be displayed or presented to users in content panels that include formatting, styling, brand images, advertisements, or the like, that may be unrelated to the content. Accordingly, in some embodiments, offering engines may be arranged to identify the content body such that the content body may be considered to be limited to actual article, blog post, report, or the like, excluding portions of the content panel that may be unrelated to the main article or post.

In some embodiments, offering engines may be arranged to employ content models that are trained or tuned to extract content from content panels. In some embodiments, content embedded/included in content panels may be marked or tagged (e.g., using particular CSS classes, IDs, or the like) to enable easy determination.

In some embodiments, content may be kept in a content management system that enables offering engines to access the content directly absent the remainder of the content panel. Accordingly, in some embodiments, offering engines may be arranged to be integrated or otherwise configured to pull content directly from content management systems that include the content.

Note, one of the ordinary skills in the art will appreciate there may be many different ways of including content in content panels. Accordingly, in some embodiments, offering engines may be arranged to employ one or more libraries, instructions, rules, pattern matching, or the like, provided via configuration information to account for different methods of including content in content panels. Further, in some embodiments, offering engines may be arranged to support adaptation to different types of content embedding or different content sources that may be encountered. Accordingly, in some embodiments, offering engines may be arranged to support the inclusion of additional libraries, instructions, rules, pattern matching, or the like, to adapt to encountered content embedding or content delivery methods.

At block 1206, in one or more of the various embodiments, offering engines may be arranged to embed some or all of the content body in a prompt or other input container.

In some embodiments, offering engines may be arranged to select one or more prompts that may be directed to determining subjects from content. In some embodiments, offering engines may be configured to employ particular machine learning systems or large language models that may require particularly formatted prompts. In some embodiments, offering engines may be arranged to be configured to select prompts based on the underlying generative artificial intelligence system or other service that may be employed for determined subjects included in the content. Accordingly, in some embodiments, offering engines may be arranged to employ configuration information to select the particular prompts that may be associated with tools or services that may be employed to determine the subjects included in the content.

For example, in some embodiments, offering engines may be arranged to enable healthcare organizations to select (or restrict) one or more large language model services to employ for determining subjects from content based on privacy concerns, pricing, or the like. Further, in some embodiments, healthcare service platforms may be arranged to include private large language models, or the like, that may be employed for determining subjects included in content.

For example, if the prompt may be directed to a large language model, the prompt may be templated, or the like, that enables the content to be embedded into the prompt.

At block 1208, in one or more of the various embodiments, offering engines may be arranged to submit the prompt to a subject model. In some embodiments, if the prompt may be prepared, offering engines may be arranged to submit them to the subject model via one or more APIs or interfaces.

At block 1210, in one or more of the various embodiments, offering engines may be arranged to determine the subject of the content based on a response from the subject model. In some embodiments, subject models may be configured to generate a response that includes one or more subjects that were determined from the content. In some embodiments, some subject models may be arranged to return more than one ranked subject or otherwise associated with one or more weighted scores or confidence scores. Accordingly, in some embodiments, offering engines may be configured to select one or more of the determined subjects as represent the subject(s) included in the content.

Next, in one or more of the various embodiments, control may be returned to a calling process.

Figure 13:
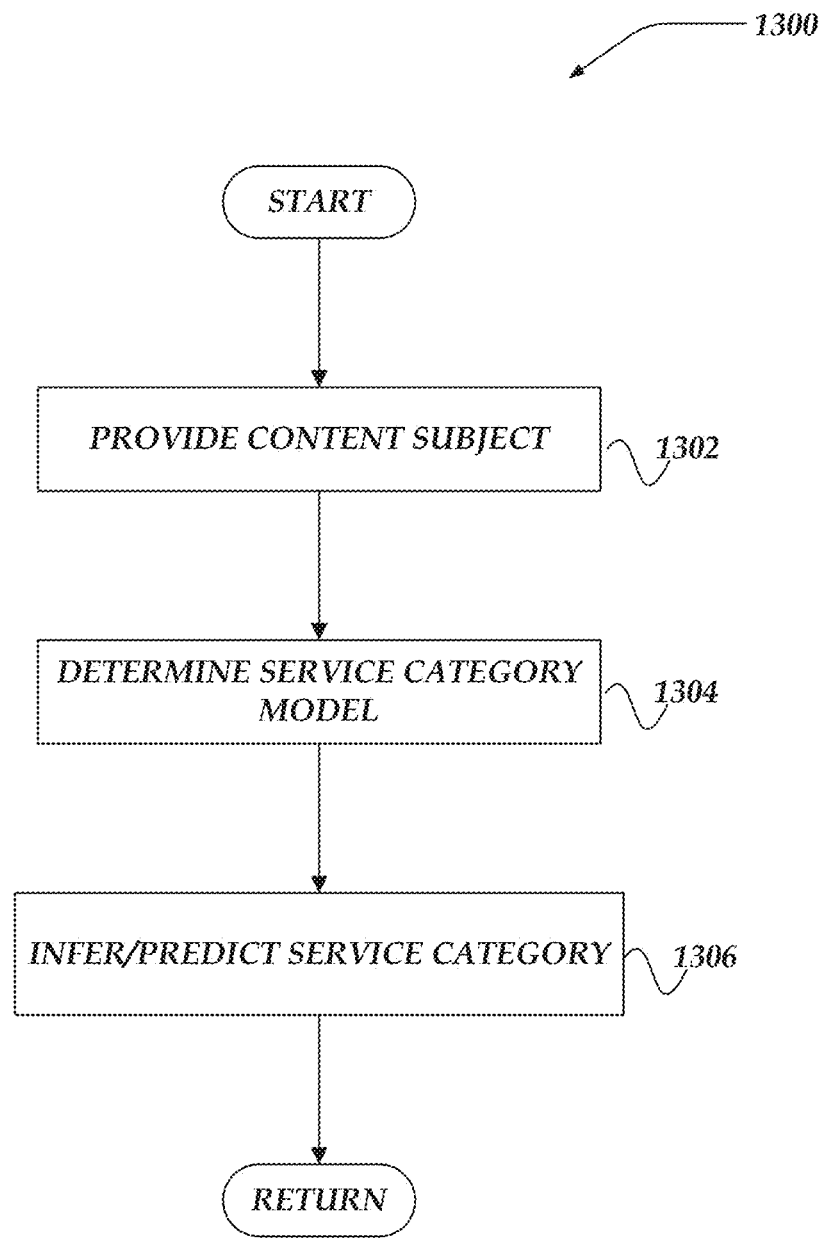
FIG. 13 illustrates a flowchart of a process for generating service offerings based on associated content and historical data in accordance with one or more of the various embodiments.

FIG. 13 illustrates a flowchart of process 1300 for generating service offerings based on associated content and historical data in accordance with one or more of the various embodiments. After a start block, at block 1302, in one or more of the various embodiments, offering engines may be provided a subject from content. In some embodiments, as described above, offering engines may be arranged to determine one or more subjects associated with content. Accordingly, in some embodiments, offering engines may be arranged to determine one or more service categories that may be related to the subjects. However, in some embodiments, subjects provided or determined from content may not directly match the services or service categories provided by a healthcare provider. Further, in some embodiments, different healthcare providers may categorize services differently than others. For example, some healthcare providers may use broader categories than other healthcare providers. Accordingly, in some embodiments, offering engines may be arranged to employ subject-category models that map subjects determined from content to service categories supported or offered by particular healthcare providers.

At block 1304, in one or more of the various embodiments, offering engines may be arranged to determine a subject-category model for the subject. In one or more of the various embodiments, offering engines may be arranged to enable different healthcare providers to configure or customize subject-category models to reflect their particular visit offerings. In some embodiments, subject-category models may be configured to employ NLP, or the like, to map words or phrases representing subjects to particular service categories.

Accordingly, in some embodiments, offering engines may be arranged to provide the subject information to the determined subject-category model via APIs or interfaces.

At block 1306, in one or more of the various embodiments, offering engines may be arranged to infer or predict one or more service categories based on the subject. In some embodiments, subject-category models may be configured to generate responses that include one or more service categories that map to the provided subjects. In some embodiments, subject-category models may be configured to return more than one subject-category. In some embodiments, if there may be multiple matching service categories, they may be associated with confidence scores that represent the quality of the match. Accordingly, in some embodiments, offering engines may be arranged to accept one or more service categories that may be associated with a confidence score that exceeds a definable threshold value.

In some embodiments, service categories may cover overlapping subjects or be arranged into a hierarchy such that a provided subject may be mapped to a broad top-level service category as well as one or more narrower categories. Accordingly, in some embodiments, offering engines may be arranged to select the narrower category if its confidence level exceeds a threshold value while the broader category may be determined if the confidence level associated with the narrower categories may be too low.

In some embodiments, the selected service categories may be included in the input records that may be provided to offering models for determining offering profile or offering panels for display to users/patients.

Next, in one or more of the various embodiments, control may be returned to a calling process.

Figure 14:
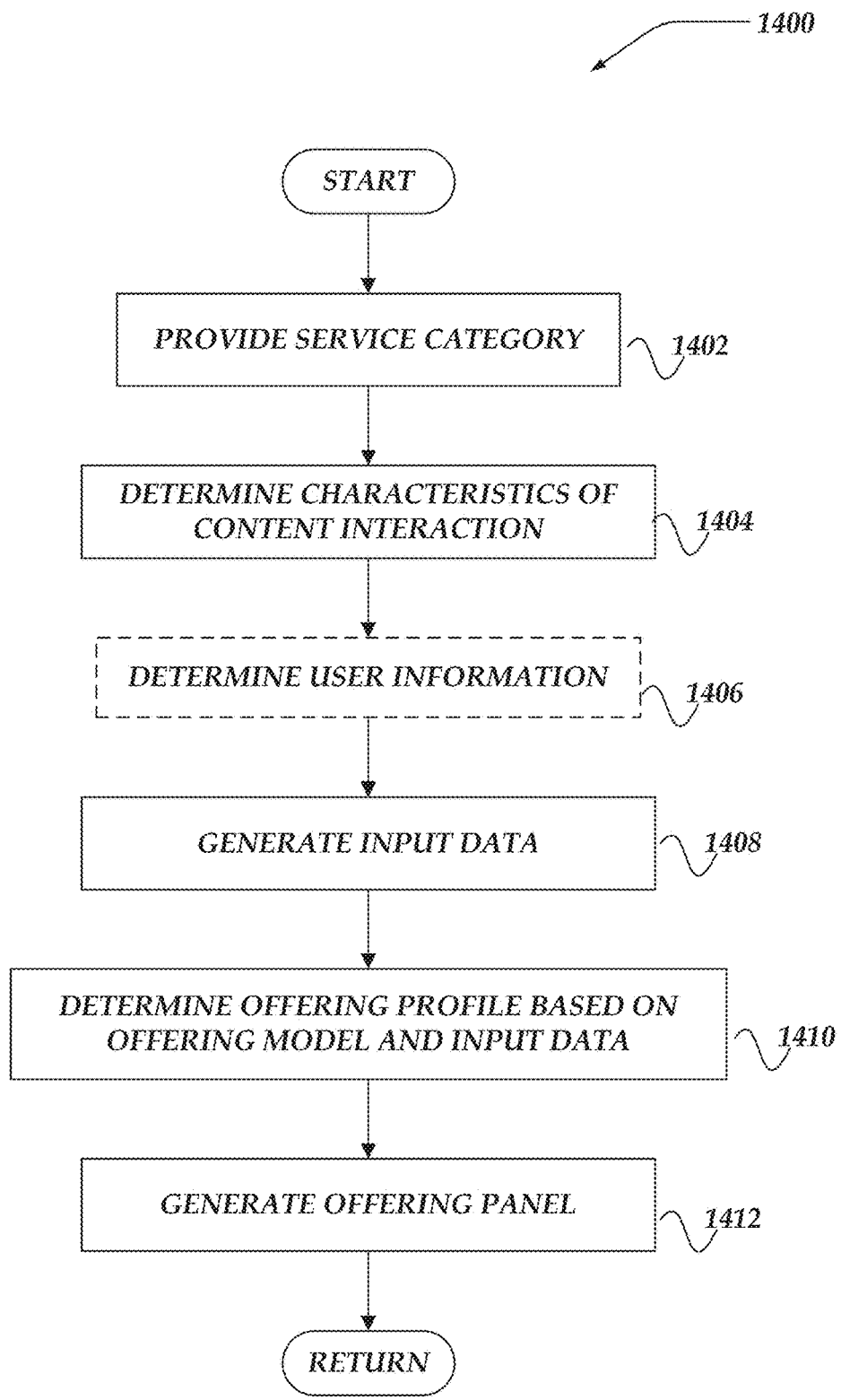
FIG. 14 illustrates a flowchart of a process for generating service offerings based on associated content and historical data in accordance with one or more of the various embodiments.

FIG. 14 illustrates a flowchart of process 1400 for generating service offerings based on associated content and historical data in accordance with one or more of the various embodiments. After a start block, at block 1402, in one or more of the various embodiments, a service category may be provided to an offering engine. As described above, in some embodiments, offering engines may be arranged to determine one or more service categories based on the subjects included in the content.

At block 1404, in one or more of the various embodiments, offering engines may be arranged to determine characteristics of the content interaction. In some embodiments, other characteristics or the content interactions may vary depending on how or where the content may be hosted/presented. In some embodiments, such characteristics may include information associated with the source of content such as original URL, author information, publication date, size of content (e.g., number of words/pages), register level (e.g., targeted education level or assumed level of subject matter knowledge of audience, or the like), language, geo-location of access, date-time of interaction, or the like. Also, in some embodiments, there may be additional or customized meta-data included in content or content panels by healthcare service platform or healthcare organizations that may be collected as well as.

In some embodiments, offering engines may be arranged to employ filters, instructions, rules, pattern matching, or the like, provided via to account for local requirements or local circumstances. Accordingly, in some embodiments, offering engines may be arranged to enable healthcare service platforms or healthcare organizations or configured content to include particular meta-data that may be employed if generating offering panels or monitoring user interactions with offering panels.

At block 1406, in one or more of the various embodiments, optionally, offering engines may be arranged to user information associated with the content interaction.

As mentioned above, in some cases, users interacting with content may be authenticated as patients of a healthcare provider. Accordingly, in some embodiments, offering engines may be arranged to enable healthcare organizations to configure which patient information may be employed as part of generating offering profiles or offering panels. For example, in some embodiments, offering engines may be configured to employ patient information such as last visit, last provider visited, category of last visits, insurance carrier, or the like, to inform the offering panels generation process.

Note, this block is indicated as being optional because in some cases for some embodiments user/patient information may be unavailable.

At block 1408, in one or more of the various embodiments, offering engines may be arranged to generate input records for generating service offerings based on associated content and historical data. As described above, in some embodiments, offering engines may be arranged to generate input records structures that may include the information detailed above. In some embodiments, input records may be configured to conform to requirements of offering models. For example, input data may be formatted as a vector, or the like, for submission to offering models.

At block 1410, in one or more of the various embodiments, offering engines may be arranged to determine one or more offering profiles based on the offering model and input records.

As described above, in some embodiments, offering models may be arranged to generate responses that include various fields or values that may be interpreted for generating offering panels. In some embodiments, offering profiles may include one or more fields that may be hidden or otherwise not recommended for display to users in offering panels. However, in some embodiments, including these hidden fields in offering profiles may enable improved analytical analysis of predicted results.

In some embodiments, offering profiles may be configured to include the labels, descriptions or narratives describing the offering as well as information for formatting the styling, layout, or user interface controls associated with offering panels.

At block 1412, in one or more of the various embodiments, offering engines may be arranged to generate one or more offering panels. In some embodiments, offering engines may be arranged to employ the information included in offering profiles to generate offering panels that conform to the formats or protocol of the hosted content or the content server. For example, if the content panel may be a HTML page, the offering panel may be integrated into the content panel by embedding HTML or DOM manipulation in the content panel.

Further, in some embodiments, offering engines may be arranged to store a record of the input record and offering profile such that they may be used for subsequent analysis. Thus, in some embodiments, offering engines may be arranged to enable particular offering panels or user interaction with individual offering panels to be traced back to the input record or offering profile that may have been used to generate the offering panels.

Figure 15:
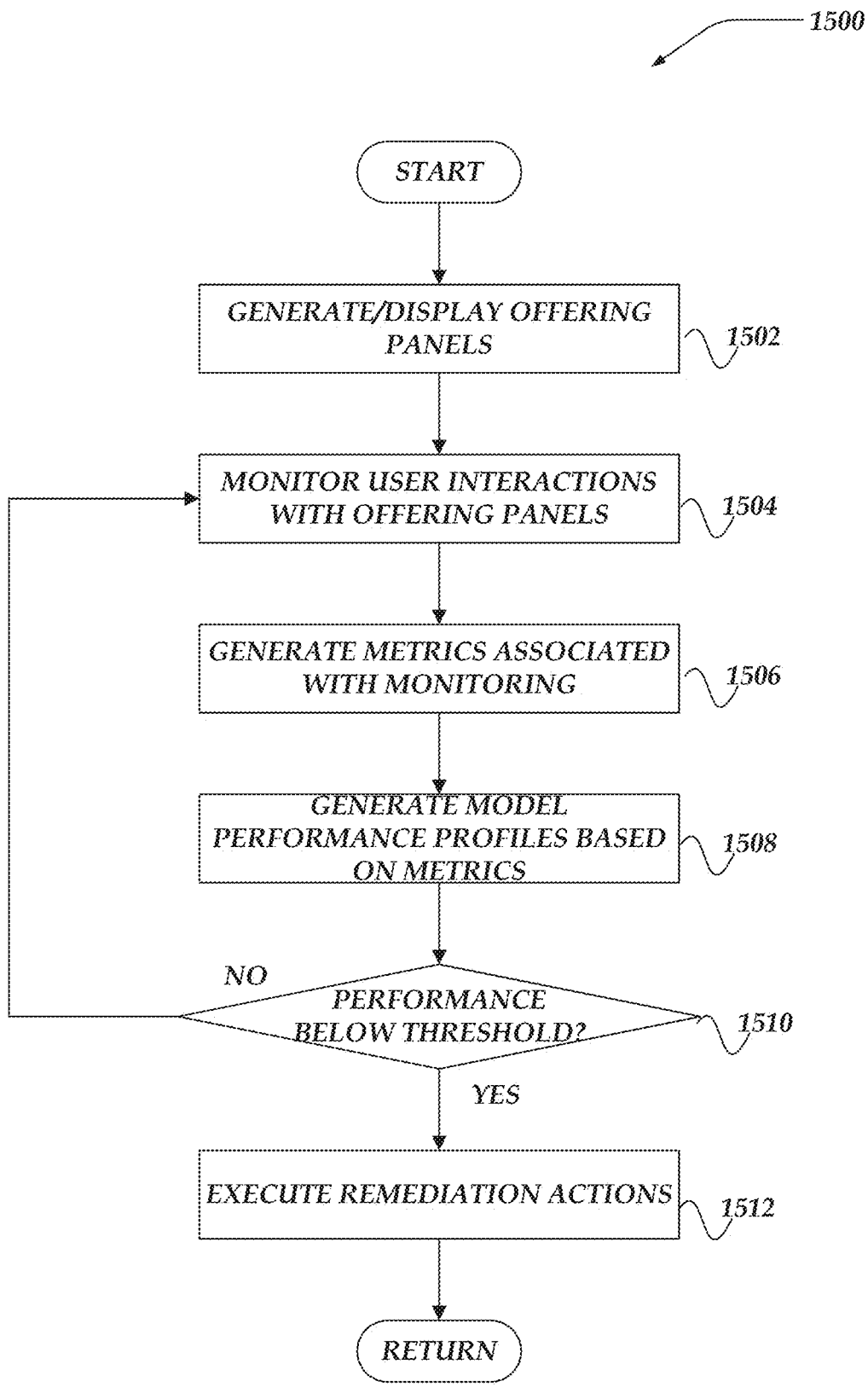
FIG. 15 illustrates a flowchart of a process for generating service offerings based on associated content and historical data in accordance with one or more of the various embodiments.

Next, in one or more of the various embodiments, control may be returned to a calling process FIG. 15 illustrates a flowchart of process 1500 for generating service offerings based on associated content and historical data in accordance with one or more of the various embodiments. After a start block, at block 1502, in one or more of the various embodiments, offering engines may be arranged to generate one or more offering panels. As described above, in some embodiments, offering engines may be arranged to generate offering profiles that may be employed to generate interactive offering panels that offer visits or appointments along-side or otherwise associated with content displayed in a content panel.

At block 1504, in one or more of the various embodiments, offering engines may be arranged to monitor user interactions with offering panels. In some embodiments, offering engines may be arranged to track various user/patient interactions with offering panels as well as if the users/patients follow through with visit appointments. Further, in some embodiments, offering engines may be arranged to track the one or more metrics associated with agreed to visits. For example, in some embodiments, offering engines may be arranged to track if the offered and accepted visit was appropriate for the patient.

Also, in some embodiments, offering engines may be arranged to provide interactive surveys to patients or providers to obtain feedback regarding the efficacy of offering panels. For example, in some embodiments, a provider survey may include questions that enable providers to identify if the offered (and accepted) visit was appropriate for the patient or appropriate with respect to the associated content.

In some embodiments, offering engines may be arranged to monitor survey results to identify high quality offering panels. Accordingly, in some embodiments, the input records, offering profiles, or the like, associated with high quality offering panels may be selected for inclusion in training data for use in subsequent automatic retraining or evaluation of offering models. Note, in some embodiments, offering engines may be arranged to mask sensitive information or otherwise de-identify information selected for including as training data.

At block 1506, in one or more of the various embodiments, offering engines may be arranged to generate one or more metrics associated with user interactions. Accordingly, in some embodiments, as users/patients interact with offering panels, including ignoring or disregarding offering panels, offering engines may collect one or more metrics representing these interactions.

At block 1508, in one or more of the various embodiments, offering engines may be arranged to generate model performance profiles based on metrics.

In some embodiments, model performance profiles may be data structures or records that include the collected metrics, other metrics, or performance/interaction history that may represent how well offering panels may be performing. In some embodiments, performance profiles may be stored or otherwise associated the input records or offering profiles that correspond to the offering panels.

At decision block 1510, in one or more of the various embodiments, if the performance of the offering panels may be below a threshold value, control may flow to block 1512; otherwise, control may loop back to block 1504.

In some embodiments, offering engines may be arranged to enable healthcare service platform administrators or healthcare organizations to configure performance threshold values. Likewise, in some embodiments, offering engines may be arranged to enable one or more metrics to be disregarded. Likewise, one or more metrics may be configured to have more or less impact (e.g., weight values) than others.

Further, in some embodiments, offering engines may be arranged to enable administrators or providers to configure which metrics or combination of metrics may be deemed as triggers for identifying poorly performing offering panels or offering models.

At block 1512, in one or more of the various embodiments, offering engines may be arranged to execute one or more remediation actions.

In some embodiments, offering engines may be arranged to indicate that that offering models associated with poorly performing offering panels may be designated for remediation. In some embodiments, remediation may include designating one or more offering models for retraining. Likewise, in some embodiments, remediation may include discarding poorly performing models in lieu of other models.

Also, in some embodiments, remediation may include generating one or more interactive reports that enable healthcare service platform administrators to review the various input records, offering profiles, performance profiles, metrics, or the like, that may be associated with offering models indicated for remediation.

Figure 16:
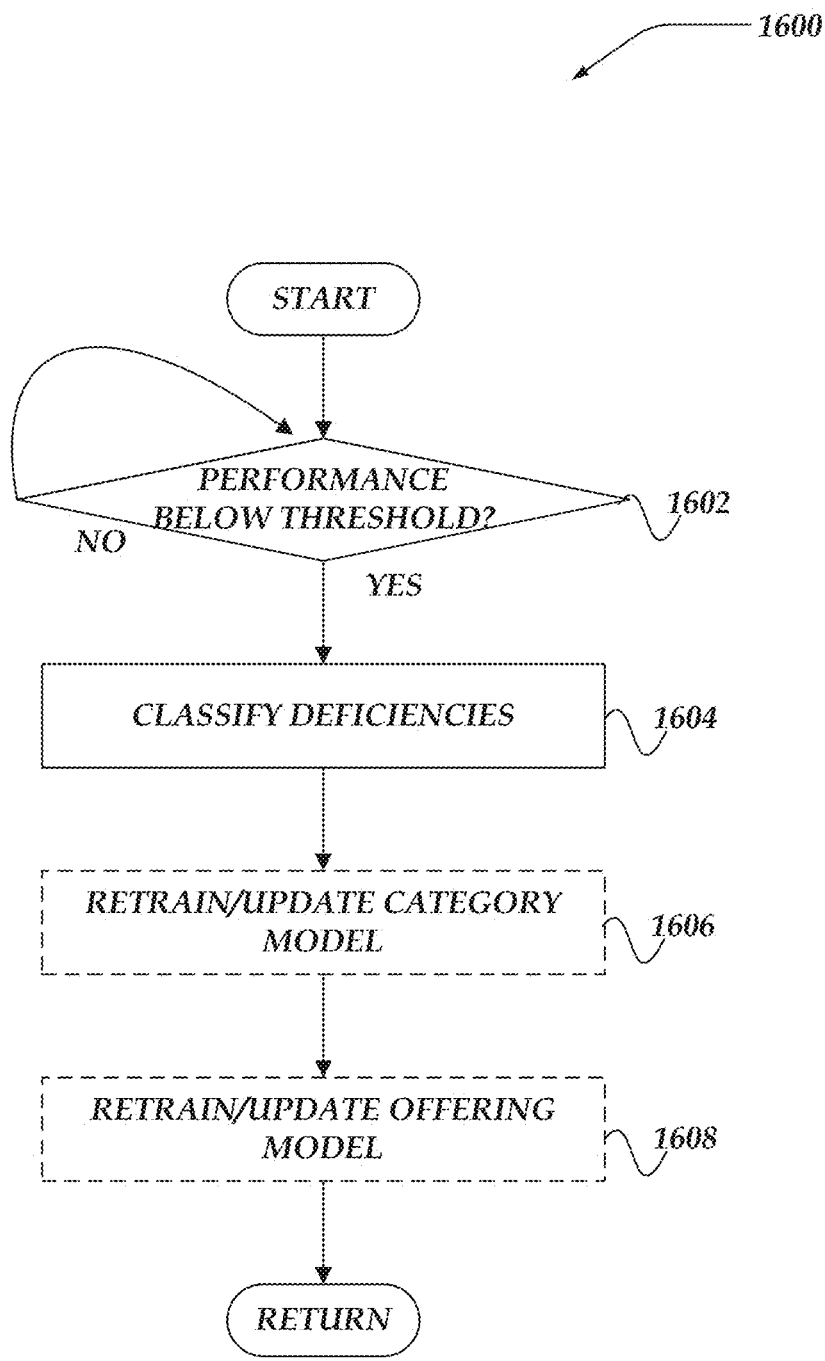
FIG. 16 illustrates a flowchart of a process for generating service offerings based on associated content and historical data in accordance with one or more of the various embodiments.

Next, in one or more of the various embodiments, control may be returned to a calling process FIG. 16 illustrates a flowchart of process 1600 for generating service offerings based on associated content and historical data in accordance with one or more of the various embodiments. After a start block, at decision block 1602, in one or more of the various embodiments, if one or more performance metrics may be below a threshold value, control may flow to block 1604; otherwise, control may loop back to decision block 1602. As mentioned above, in some embodiments, offering engines may be arranged to monitor user/patient interactions with offering panels. Also, in some embodiments, offering engines may be arranged to monitor healthcare organization, or healthcare provider interactions with offering panels. Accordingly, in some embodiments, offering engines may be arranged to establish performance profiles for offering panels, offering models, or the like. Further, in some embodiments, offering engines may be arranged to enable healthcare organizations or healthcare service platform administrators to establish one or more performance thresholds such that if metrics in performance profiles fall below configured thresholds or outside of declared ranges, the associated offering models may be indicated as deficient. Accordingly, in some embodiments, offering engines may be arranged to execute one or more remediation actions for the indicated offering models.

At block 1604, in one or more of the various embodiments, offering engines may be arranged to determine or classify one or more deficiencies. In some embodiments, the particular metrics that fall outside of acceptable ranges or below threshold values may explicitly indicate one or more sources or causes of the indicated deficiencies. For example, in some embodiments, responses to survey questions may indicate particular deficiencies. For example, a survey question may enable users to indicate if the offering panels was relevant to their interests or to the content.

Also, in some embodiments, offering engines may be arranged to employ one or more deficiency models that may include machine learning classifiers, analytical heuristics, filters, or the like, that may be employed to classify deficiencies.

For example, in some embodiments, a deficiency model may be configured to compare input records or offering profiles associated with non-deficient offering panels to input records or offering profiles associated with the deficient offering models. Accordingly, in some embodiments, offering engines may be arranged to employ deficiency models to determine one or more potential sources of the deficiencies. For example, in some embodiments, deficiency models may be configured to compare offering profiles associated with the same subjects or service categories to determine which fields in the offering profiles corresponding to deficient offering panels may be significantly different from offering profiles for the non-deficient offering panels. For example, in some embodiments, offering profiles for non-deficient offering panels may indicate that offering panels presented alongside or inline with the content (e.g., in the content panel) may have improved performance to offering panels that are displayed or accessed by link or URLs. Further, in some embodiments, deficiency models may be configured to identify if other features, such as, showing provider names, using long descriptions, font-size, panel user interface templates, or the like, result in significant performance differences.

In some embodiments, offering engines operating in multi-tenant environments (e.g., supporting more than one independent healthcare organization) may be provided to performance profiles, offering profiles, or the like, that may be associated with other healthcare providers (absent sensitive or private information). Accordingly, in some embodiments, characteristics of performant offering panels associated with different healthcare organizations may be compared or evaluated to identify one or more causes of deficient offering panels.

At block 1606, in one or more of the various embodiments, optionally, offering engines may be arranged to retrain/update subject models or subject-category models.

In some cases, the deficiencies in offering panels performance may be related to mismatches between inferred subjects/categories. For example, in some embodiments, the content subject matter, formatting, communication styles, or the like, may change such that the subject models, or subject-category models used to infer subjects or service categories may become less effective or less accurate. Accordingly, in some embodiments, offering engines may be arranged to select one or more subject models or subject-category models for retraining or discarding.

Similarly, in some embodiments, healthcare provider organizations may modify their service categories by adding or removing services. Accordingly, in some embodiments, subject-category models may become out-of-date or otherwise inaccurate in view of the service offering changes.

Accordingly in some embodiments, offering engines may be arranged to employ an updated test data set to automatically retrain subject models or subject-category models.

Note, this block is indicated as being optional because in some cases the deficiencies associated with deficient offering panels may be unrelated to subject determination or subject-category mapping.

At block 1608, in one or more of the various embodiments, optionally, offering engines may be arranged to retrain/update offering models.

In some embodiments, deficiencies with offering panels may be determined to be associated with offering models. In some embodiments, offering engines may be arranged to retrain or discard one or more offering models.

Accordingly, in some embodiments, offering engines may be arranged to automatically retrain deficient offering models using updated training data. Further, in some embodiments, offering engines may be arranged to determine input records or offering profiles for offering panels that are known to be non-deficient. Accordingly, in some embodiments. Also, in some embodiments, offering engines may be arranged to employ training models to observe if offering models trained or tested using updated training data may generate offering profiles that may be different than the deficient offering profiles.

Note, in some embodiments, offering engines may be arranged to monitor training data, such that if the training data may be updated, offering models may be automatically selected for retraining to confirm that they generate quality results using the updated training data.

Next, in one or more of the various embodiments, control may be returned to a calling process.

It will be understood that each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multi-processor computer system. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware-based systems, which perform the specified actions or steps, or combinations of special purpose hardware and computer instructions. The foregoing example should not be construed as limiting or exhaustive, but rather, an illustrative use case to show an implementation of at least one of the various embodiments of the invention.

Further, in one or more embodiments (not shown in the figures), the logic in the illustrative flowcharts may be executed using an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. In one or more embodiments, a microcontroller may be arranged to directly execute its own embedded logic to perform actions and access its own internal memory and its own external Input and Output Interfaces (e.g., hardware pins or wireless transceivers) to perform actions, such as System On a Chip (SOC), or the like.

What is claimed as new and desired to be protected by Letters Patent of the United States is:

1. A method for generating service offerings in a computing environment using one or more processors to execute instructions that are configured to cause actions, comprising:
    determining content from a content panel based on one or more of a markup language, an encoding, or a format associated with the content panel;
    determining one or more subjects associated with the content based on information included in the content and one or more evaluations of the content by a subject model;
    determining a service category associated with the one or more subjects based on one or more services provided by a healthcare organization;
    employing an offering model to generate an offering panel based on the service category and an availability of the one or more services, wherein the offering panel displays information associated with an available service, wherein the offering model includes a machine learning model;
    evaluating the offering model based on monitoring one or more physical interactions between one or more of users and the offering panel;
    employing one or more results of the evaluation to perform further actions, including:
        designating the offering model for retraining based on the one or more performance metrics falling below a threshold value;
        retraining the designated offering model based on one or more other metrics associated with one or more other offering models and a training model, wherein the training model includes one or more of a machine learning model or a large language model; and
        employing the retrained offering model to generate one or more other offering panels for display to the one or more users; and
    employing a deficiency model to compare the one or more physical interactions of the one or more users with the one or more offering panels to one or more previous physical interactions of the one or more users with one or more deficient offering panels; and
    employing the comparison to determine one or more potential sources that improve relevance of the one or more offering panels for the one or more users and identify one or more causes of relevance deficiency for the one or more users.

2. The method of claim 1, further comprising:
    modifying the content in the content panel to include one or more links or references to the offering panel, wherein activating the link or reference displays the offering panel separate from the content panel.

3. The method of claim 1, wherein generating the offering panel, further comprises:
    determining a portion of the one or more users that are patients of the healthcare organization based on authenticating the portion of the one or more users with the healthcare organization;
    determining patient information for the authenticated portion of the one or more users from the healthcare organization, wherein the patient information includes one or more of demographic information, a date of a previous visit, insurance information, a provider visited during a previous visit, a service category associated with a previous visit, or a patient profile; and
    providing the patient information to the offering model.

4. The method of claim 1, wherein determining the one or more subjects associated with the content, further comprises:
  generating a prompt that includes one or more portions of the content for evaluation by the subject model that includes one or more large language models; and
  determining the one or more subjects based on a response provided by the subject model.

5. The method of claim 1, wherein determining the service category associated with the one or more subjects, further comprises:
  determining a plurality of service categories based on a plurality of services offered by the healthcare organization; and
  employing a subject-category model to determine the plurality of service categories based on one or more matches of the one or more subjects with the one or more service categories.

6. The method of claim 1, wherein generating the offering panel further comprises:
  determining one or more available services associated with the service category;
  prioritizing the one or more available services based on one or more type of visit, an availability of providers, a utilization of providers, or a location of a clinic, wherein the type of visit includes one or more of a remote visit or an in-person visit; and
  generating one or more user interface controls that enables the user to request a visit associated with the one or more the available services, wherein the one or more available services are sorted or redacted based on the prioritization of the one or more available services.

7. The method of claim 1, further comprising:
  determining one or more non-deficient offering panels based on one or more physical interaction metrics that exceed one or more defined threshold values;
  determining input data and one or more offering profiles associated with the one or more non-deficient offering panels;
  updating training data to include the determined input data and determined one or more offering profiles; and
  employing the updated training data to retrain the offering model that is designated for retraining.

8. A network computer for generating service offerings, comprising:
  a memory that stores at least instructions; and
  one or more processors that execute instructions that are configured to cause actions, including:
    determining content from a content panel based on one or more of a markup language, an encoding, or a format associated with the content panel;
    determining one or more subjects associated with the content based on information included in the content and one or more evaluations of the content by a subject model;
    determining a service category associated with the one or more subjects based on one or more services provided by a healthcare organization;
    employing an offering model to generate an offering panel based on the service category and an availability of the one or more services, wherein the offering panel displays information associated with an available service, wherein the offering model includes a machine learning model;
    evaluating the offering model based on monitoring one or more physical interactions between one or more of users and the offering panel;
    employing one or more results of the evaluation to perform further actions, including:
      designating the offering model for retraining based on the one or more performance metrics falling below a threshold value;
      retraining the designated offering model based on one or more other metrics associated with one or more other offering models and a training model, wherein the training model includes one or more of a machine learning model or a large language model; and
      employing the retrained offering model to generate one or more other offering panels for display to the one or more users; and
    employing a deficiency model to compare the one or more physical interactions of the one or more users with the one or more offering panels to one or more previous physical interactions of the one or more users with one or more deficient offering panels; and
    employing the comparison to determine one or more potential sources that improve relevance of the one or more offering panels for the one or more users and identify one or more causes of relevance deficiency for the one or more users.

9. The network computer of claim 8, wherein the one or more processors execute instructions that are configured to cause actions, further comprising:
  modifying the content in the content panel to include one or more links or references to the offering panel, wherein activating the link or reference displays the offering panel separate from the content panel.

10. The network computer of claim 8, wherein generating the offering panel, further comprises:
  determining a portion of the one or more users that are patients of the healthcare organization based on authenticating the portion of the one or more users with the healthcare organization;
  determining patient information for the authenticated portion of the one or more users from the healthcare organization, wherein the patient information includes one or more of demographic information, a date of a previous visit, insurance information, a provider visited during a previous visit, a service category associated with a previous visit, or a patient profile; and
  providing the patient information to the offering model.

11. The network computer of claim 8, wherein determining the one or more subjects associated with the content, further comprises:
  generating a prompt that includes one or more portions of the content for evaluation by the subject model that includes one or more large language models; and
  determining the one or more subjects based on a response provided by the subject model.

12. The network computer of claim 8, wherein determining the service category associated with the one or more subjects, further comprises:
  determining a plurality of service categories based on a plurality of services offered by the healthcare organization; and
  employing a subject-category model to determine the plurality of service categories based on one or more matches of the one or more subjects with the one or more service categories.

13. The network computer of claim 8, wherein generating the offering panel further comprises:
  determining one or more available services associated with the service category;

prioritizing the one or more available services based on one or more a type of visit, an availability of providers, a utilization of providers, or a location of a clinic, wherein the type of visit includes one or more of a remote visit or an in-person visit; and generating one or more user interface controls that enables the user to request a visit associated with the one or more the available services, wherein the one or more available services are sorted or redacted based on the prioritization of the one or more available services.

14. The network computer of claim 8, wherein the one or more processors execute instructions that are configured to cause actions, further comprising:

determining one or more non-deficient offering panels based on one or more physical interaction metrics that exceed one or more defined threshold values;

determining input data and one or more offering profiles associated with the one or more non-deficient offering panels;

updating training data to include the determined input data and determined one or more offering profiles; and employing the updated training data to retrain the offering model that is designated for retraining.

15. A processor readable non-transitory media that includes instructions configured for generating service offerings, wherein execution of the instructions by one or more processors on one or more network computers performs actions, comprising:

determining content from a content panel based on one or more of a markup language, an encoding, or a format associated with the content panel;

determining one or more subjects associated with the content based on information included in the content and one or more evaluations of the content by a subject model;

determining a service category associated with the one or more subjects based on one or more services provided by a healthcare organization;

employing an offering model to generate an offering panel based on the service category and an availability of the one or more services, wherein the offering panel displays information associated with an available service, wherein the offering model includes a machine learning model;

evaluating the offering model based on monitoring one or more physical interactions between one or more of users and the offering panel;

employing one or more results of the evaluation to perform further actions, including:

designating the offering model for retraining based on the one or more performance metrics falling below a threshold value;

retraining the designated offering model based on one or more other metrics associated with one or more other offering models and a training model, wherein the training model includes one or more of a machine learning model or a large language model; and employing the retrained offering model to generate one or more other offering panels for display to the one or more users; and employing a deficiency model to compare the one or more physical interactions of the one or more users with the one or more offering panels to one or more previous physical interactions of the one or more users with one or more deficient offering panels; and employing the comparison to determine one or more potential sources that improve relevance of the one or more offering panels for the one or more users and identify one or more causes of relevance deficiency for the one or more users.

16. The media of claim 15, further comprising:

modifying the content in the content panel to include one or more links or references to the offering panel, wherein activating the link or reference displays the offering panel separate from the content panel.

17. The media of claim 15, wherein generating the offering panel, further comprises:

determining a portion of the one or more users that are patients of the healthcare organization based on authenticating the portion of the one or more users with the healthcare organization;

determining patient information for the authenticated portion of the one or more users from the healthcare organization, wherein the patient information includes one or more of demographic information, a date of a previous visit, insurance information, a provider visited during a previous visit, a service category associated with a previous visit, or a patient profile; and providing the patient information to the offering model.

18. The media of claim 15, wherein determining the one or more subjects associated with the content, further comprises:

generating a prompt that includes one or more portions of the content for evaluation by the subject model that includes one or more large language models; and determining the one or more subjects based on a response provided by the subject model.

19. The media of claim 15, wherein determining the service category associated with the one or more subjects, further comprises:

determining a plurality of service categories based on a plurality of services offered by the healthcare organization; and employing a subject-category model to determine the plurality of service categories based on one or more matches of the one or more subjects with the one or more service categories.

20. The media of claim 15, wherein generating the offering panel further comprises:

determining one or more available services associated with the service category;

prioritizing the one or more available services based on one or more a type of visit, an availability of providers, a utilization of providers, or a location of a clinic, wherein the type of visit includes one or more of a remote visit or an in-person visit; and generating one or more user interface controls that enables the user to request a visit associated with the one or more the available services, wherein the one or more available services are sorted or redacted based on the prioritization of the one or more available services.

21. The media of claim 15, further comprising:

determining one or more non-deficient offering panels based on one or more physical interaction metrics that exceed one or more defined threshold values;

determining input data and one or more offering profiles associated with the one or more non-deficient offering panels;

updating training data to include the determined input data and determined one or more offering profiles; and employing the updated training data to retrain the offering model that is designated for retraining.

22. A system for generating service offerings in a computing environment:

one or more network computers, comprising:
  a memory that stores at least instructions; and
  one or more processors that execute instructions that are configured to cause actions, including:
    determining content from a content panel based on one or more of a markup language, an encoding, or a format associated with the content panel;
    determining one or more subjects associated with the content based on information included in the content and one or more evaluations of the content by a subject model;
    determining a service category associated with the one or more subjects based on one or more services provided by a healthcare organization;
    employing an offering model to generate an offering panel based on the service category and an availability of the one or more services, wherein the offering panel displays information associated with an available service, wherein the offering model includes a machine learning model;
    evaluating the offering model based on monitoring one or more physical interactions between one or more of users and the offering panel;
    employing one or more results of the evaluation to perform further actions, including:
      designating the offering model for retraining based on the one or more performance metrics falling below a threshold value;
      retraining the designated offering model based on one or more other metrics associated with one or more other offering models and a training model, wherein the training model includes one or more of a machine learning model or a large language model; and
      employing the retrained offering model to generate one or more other offering panels for display to the one or more users; and
    employing a deficiency model to compare the one or more physical interactions of the one or more users with the one or more offering panels to one or more previous physical interactions of the one or more users with one or more deficient offering panels; and
    employing the comparison to determine one or more potential sources that improve relevance of the one or more offering panels for the one or more users and identify one or more causes of relevance deficiency for the one or more users; and
one or more client computers, comprising:
  a memory that stores at least instructions; and
  one or more processors that execute instructions that are configured to cause actions, including:
  providing the content panel.

23. The system of claim 22, wherein the one or more processors of the one or more network computers execute instructions that are configured to cause actions, further comprising:
  modifying the content in the content panel to include one or more links or references to the offering panel, wherein activating the link or reference displays the offering panel separate from the content panel.

24. The system of claim 22, wherein generating the offering panel, further comprises:
  determining a portion of the one or more users that are patients of the healthcare organization based on authenticating the portion of the one or more users with the healthcare organization;
  determining patient information for the authenticated portion of the one or more users from the healthcare organization, wherein the patient information includes one or more of demographic information, a date of a previous visit, insurance information, a provider visited during a previous visit, a service category associated with a previous visit, or a patient profile; and
  providing the patient information to the offering model.

25. The system of claim 22, wherein determining the one or more subjects associated with the content, further comprises:
  generating a prompt that includes one or more portions of the content for evaluation by the subject model that includes one or more large language models; and
  determining the one or more subjects based on a response provided by the subject model.

26. The system of claim 22, wherein determining the service category associated with the one or more subjects, further comprises:
  determining a plurality of service categories based on a plurality of services offered by the healthcare organization; and
  employing a subject-category model to determine the plurality of service categories based on one or more matches of the one or more subjects with the one or more service categories.

27. The system of claim 22, wherein generating the offering panel further comprises:
  determining one or more available services associated with the service category;
  prioritizing the one or more available services based on one or more a type of visit, an availability of providers, a utilization of providers, or a location of a clinic, wherein the type of visit includes one or more of a remote visit or an in-person visit; and
  generating one or more user interface controls that enables the user to request a visit associated with the one or more the available services, wherein the one or more available services are sorted or redacted based on the prioritization of the one or more available services.

28. The system of claim 22, wherein the one or more processors of the one or more network computers execute instructions that are configured to cause actions, further comprising:
  determining one or more non-deficient offering panels based on one or more physical interaction metrics that exceed one or more defined threshold values;
  determining input data and one or more offering profiles associated with the one or more non-deficient offering panels;
  updating training data to include the determined input data and determined one or more offering profiles; and
  employing the updated training data to retrain the offering model that is designated for retraining.

* * * * *